United States Patent
Rhoades et al.

(10) Patent No.: US 10,433,793 B1
(45) Date of Patent: Oct. 8, 2019

(54) METHODS AND SYSTEMS FOR SIMULTANEOUS REVIEW OF BRAIN ACTIVITY AND PHYSICAL MANIFESTATIONS OF USERS

(71) Applicant: Cadwell Laboratories Inc., Kennewick, WA (US)

(72) Inventors: Alison Rhoades, Kennewick, WA (US); Wayne Dearing, Kennewick, WA (US); Christopher Rickard, Kennewick, WA (US)

(73) Assignee: Cadwell Laboratories, Inc., Kennewick, WA (US)

( * ) Notice: Subject to any disclaimer, the term of this patent is extended or adjusted under 35 U.S.C. 154(b) by 218 days.

(21) Appl. No.: 15/080,960

(22) Filed: Mar. 25, 2016

Related U.S. Application Data

(60) Provisional application No. 62/139,151, filed on Mar. 27, 2015.

(51) Int. Cl.
*A61B 5/0476* (2006.01)
*A61B 5/00* (2006.01)

(52) U.S. Cl.
CPC ............ *A61B 5/743* (2013.01); *A61B 5/0476* (2013.01); *A61B 5/4094* (2013.01); *A61B 5/7275* (2013.01); *A61B 5/742* (2013.01)

(58) Field of Classification Search
CPC .............................. A61B 5/743; A61B 5/7435
See application file for complete search history.

(56) References Cited

U.S. PATENT DOCUMENTS

| | | |
|---|---|---|
| 751,475 A | 2/1904 | De Vilbiss |
| 2,320,709 A | 6/1943 | Arnesen |
| 2,807,259 A | 9/1957 | Guerriero |
| 3,682,162 A | 8/1972 | Colyer |
| 3,985,125 A | 10/1976 | Rose |
| 4,155,353 A | 5/1979 | Rea |
| 4,263,899 A | 4/1981 | Burgin |
| 4,545,374 A | 10/1985 | Jacobson |
| 4,562,832 A | 1/1986 | Wilder |
| 4,616,635 A | 10/1986 | Caspar |

(Continued)

FOREIGN PATENT DOCUMENTS

| | | |
|---|---|---|
| EP | 298268 | 1/1989 |
| EP | 890341 | 1/1999 |

(Continued)

OTHER PUBLICATIONS

"Software for Electroencephalogram Acquisition and Processing 'WinEEG,'" Version 2.8. 2009. 277 pages.*

(Continued)

*Primary Examiner* — Meredith Weare
(74) *Attorney, Agent, or Firm* — Novel IP

(57) ABSTRACT

Methods and systems are disclosed for a guidance application that allows a practitioner to easily correlate a fluctuation in any channel of a plurality of channels constituting received electroencephalography ("EEG") data to a particular physical manifestation. For example, the guidance application automatically synchronizes incoming EEG data to the physical manifestations and allows for automatic retrieval a portion of video data (e.g., of the physical manifestation) that corresponds to a selected portion of EEG data.

20 Claims, 31 Drawing Sheets

(56) References Cited

U.S. PATENT DOCUMENTS

| | | |
|---|---|---|
| 4,705,049 A | 11/1987 | John |
| 4,716,901 A | 1/1988 | Jackson |
| 4,765,311 A | 8/1988 | Kulik |
| 4,817,587 A | 4/1989 | Janese |
| 4,862,891 A | 9/1989 | Smith |
| 5,171,279 A | 12/1992 | Mathews |
| 5,196,015 A | 3/1993 | Neubardt |
| 5,284,153 A | 2/1994 | Raymond |
| 5,284,154 A | 2/1994 | Raymond |
| 5,299,563 A | 4/1994 | Seton |
| 5,377,667 A | 1/1995 | Patton |
| 5,472,426 A | 12/1995 | Bonati |
| 5,474,558 A | 12/1995 | Neubardt |
| 5,540,235 A | 7/1996 | Wilson |
| 5,560,372 A | 10/1996 | Cory |
| 5,565,779 A | 10/1996 | Arakawa |
| 5,601,608 A | 2/1997 | Mouchawar |
| 5,681,265 A | 10/1997 | Maeda |
| 5,728,046 A | 3/1998 | Mayer |
| 5,741,261 A | 4/1998 | Moskovitz |
| 5,772,661 A | 6/1998 | Michelson |
| 5,775,331 A | 7/1998 | Raymond |
| 5,785,648 A | 7/1998 | Min |
| 5,792,044 A | 8/1998 | Foley |
| 5,795,291 A | 8/1998 | Koros |
| 5,798,798 A * | 8/1998 | Rector .............. G06F 19/3418 348/476 |
| 5,830,150 A | 11/1998 | Palmer |
| 5,860,973 A | 1/1999 | Michelson |
| 5,868,668 A | 2/1999 | Weiss |
| 5,885,210 A | 3/1999 | Cox |
| 5,891,147 A | 4/1999 | Moskovitz |
| 5,928,139 A | 7/1999 | Koros |
| 5,928,158 A | 7/1999 | Aristides |
| 5,931,777 A | 8/1999 | Sava |
| 5,944,658 A | 8/1999 | Koros |
| 5,954,635 A | 9/1999 | Foley |
| 5,993,385 A | 11/1999 | Johnston |
| 6,004,312 A | 12/1999 | Finneran |
| 6,004,341 A | 12/1999 | Zhu |
| 6,042,540 A | 3/2000 | Johnston |
| 6,074,343 A | 6/2000 | Nathanson |
| 6,095,987 A | 8/2000 | Shmulewitz |
| 6,139,493 A | 10/2000 | Koros |
| 6,152,871 A | 11/2000 | Foley |
| 6,181,961 B1 | 1/2001 | Prass |
| 6,196,969 B1 | 3/2001 | Bester |
| 6,206,826 B1 | 3/2001 | Mathews |
| 6,224,545 B1 | 5/2001 | Cocchia |
| 6,259,945 B1 | 7/2001 | Epstein |
| 6,266,558 B1 | 7/2001 | Gozani |
| 6,287,322 B1 | 9/2001 | Zhu |
| 6,302,842 B1 | 10/2001 | Auerbach |
| 6,306,100 B1 | 10/2001 | Prass |
| 6,309,349 B1 | 10/2001 | Bertolero |
| 6,325,764 B1 | 12/2001 | Griffith |
| 6,334,068 B1 | 12/2001 | Hacker |
| 6,425,859 B1 | 7/2002 | Foley |
| 6,450,952 B1 | 9/2002 | Rioux |
| 6,466,817 B1 | 10/2002 | Kaula |
| 6,500,128 B2 | 12/2002 | Marino |
| 6,535,759 B1 | 3/2003 | Epstein |
| 6,609,018 B2 | 8/2003 | Cory |
| 6,712,795 B1 | 3/2004 | Cohen |
| 6,805,668 B1 | 10/2004 | Cadwell |
| 6,847,849 B2 | 1/2005 | Mamo |
| 6,851,430 B2 | 2/2005 | Tsou |
| 6,870,109 B1 | 3/2005 | Villarreal |
| 6,926,728 B2 | 8/2005 | Zucherman |
| 6,945,933 B2 | 9/2005 | Branch |
| 7,072,521 B1 | 7/2006 | Cadwell |
| 7,089,059 B1 | 8/2006 | Pless |
| 7,104,965 B1 | 9/2006 | Jiang |
| 7,177,677 B2 | 2/2007 | Kaula |
| 7,214,197 B2 | 5/2007 | Prass |
| 7,230,688 B1 | 6/2007 | Villarreal |
| 7,261,688 B2 | 8/2007 | Smith |
| 7,374,448 B1 | 5/2008 | Jepsen |
| 7,470,236 B1 | 12/2008 | Kelleher |
| 7,522,953 B2 | 4/2009 | Kaula |
| 7,713,210 B2 | 5/2010 | Byrd |
| 7,801,601 B2 | 9/2010 | Maschino |
| 7,914,350 B1 | 3/2011 | Bozich |
| 7,963,927 B2 | 6/2011 | Kelleher |
| 7,983,761 B2 | 7/2011 | Giuntoli |
| 8,147,421 B2 | 4/2012 | Farquhar |
| 8,160,694 B2 | 4/2012 | Salmon |
| 8,192,437 B2 | 6/2012 | Simonson |
| D670,656 S | 11/2012 | Jepsen |
| 8,323,208 B2 | 12/2012 | Davis |
| 8,876,813 B2 | 11/2014 | Min |
| 8,942,797 B2 | 1/2015 | Bartol |
| 8,958,869 B2 | 2/2015 | Kelleher |
| 9,084,551 B2 | 7/2015 | Brunnett |
| 9,155,503 B2 | 10/2015 | Cadwell |
| 9,295,401 B2 | 3/2016 | Cadwell |
| 9,352,153 B2 | 5/2016 | Van Dijk |
| 9,730,634 B2 | 8/2017 | Cadwell |
| 2002/0007188 A1 | 1/2002 | Arambula |
| 2002/0095080 A1 | 7/2002 | Cory |
| 2003/0045808 A1 | 3/2003 | Kaula |
| 2004/0263353 A1 * | 12/2004 | Imajo .............. A61B 5/0476 340/870.07 |
| 2005/0075578 A1 | 4/2005 | Gharib |
| 2005/0182454 A1 | 8/2005 | Gharib |
| 2006/0009754 A1 | 1/2006 | Boese |
| 2006/0085048 A1 | 4/2006 | Cory |
| 2006/0085049 A1 | 4/2006 | Cory |
| 2006/0122514 A1 | 6/2006 | Byrd |
| 2006/0258951 A1 | 11/2006 | Bleich |
| 2007/0016097 A1 | 1/2007 | Farquhar |
| 2007/0021682 A1 | 1/2007 | Gharib |
| 2007/0032841 A1 | 2/2007 | Urmey |
| 2007/0049962 A1 | 3/2007 | Marino |
| 2007/0184422 A1 | 8/2007 | Takahashi |
| 2008/0027507 A1 | 1/2008 | Bijelic |
| 2008/0058606 A1 | 3/2008 | Miles |
| 2008/0065144 A1 | 3/2008 | Marino |
| 2008/0071191 A1 | 3/2008 | Kelleher |
| 2008/0082136 A1 | 4/2008 | Gaudiani |
| 2008/0097164 A1 | 4/2008 | Miles |
| 2008/0167574 A1 | 7/2008 | Farquhar |
| 2008/0194970 A1 | 8/2008 | Steers |
| 2008/0269777 A1 | 10/2008 | Appenrodt |
| 2008/0281313 A1 | 11/2008 | Fagin |
| 2009/0018399 A1 | 1/2009 | Martinelli |
| 2009/0088660 A1 | 4/2009 | McMorrow |
| 2009/0105604 A1 | 4/2009 | Bertagnoli |
| 2009/0177112 A1 | 7/2009 | Gharib |
| 2009/0204016 A1 | 8/2009 | Gharib |
| 2009/0209879 A1 | 8/2009 | Kaula |
| 2009/0259108 A1 | 10/2009 | Miles |
| 2009/0279767 A1 | 11/2009 | Kukuk |
| 2010/0036384 A1 | 2/2010 | Gorek |
| 2010/0106011 A1 | 4/2010 | Byrd |
| 2010/0152604 A1 | 6/2010 | Kaula |
| 2010/0286554 A1 | 11/2010 | Davis |
| 2010/0317989 A1 | 12/2010 | Gharib |
| 2011/0082383 A1 | 4/2011 | Cory |
| 2011/0184308 A1 | 7/2011 | Kaula |
| 2011/0201911 A1 * | 8/2011 | Johnson .............. A61B 5/14532 600/365 |
| 2011/0218820 A1 * | 9/2011 | Himes .............. G06F 19/3406 705/3 |
| 2011/0295579 A1 | 12/2011 | Tang |
| 2011/0313530 A1 | 12/2011 | Gharib |
| 2012/0109000 A1 | 5/2012 | Kaula |
| 2012/0109004 A1 | 5/2012 | Cadwell |
| 2012/0220891 A1 | 8/2012 | Kaula |
| 2012/0238855 A1 * | 9/2012 | Lanning .............. A61B 5/0006 600/378 |
| 2012/0238893 A1 | 9/2012 | Farquhar |
| 2012/0296230 A1 | 11/2012 | Davis |

(56) References Cited

U.S. PATENT DOCUMENTS

| | | | |
|---|---|---|---|
| 2013/0303933 A1* | 11/2013 | Bonnstetter | A61B 5/0476 600/544 |
| 2014/0121555 A1 | 5/2014 | Scott | |
| 2014/0275926 A1 | 9/2014 | Scott | |
| 2016/0000382 A1 | 1/2016 | Jain | |
| 2016/0128593 A1* | 5/2016 | Sinharay | A61B 5/04014 600/544 |
| 2016/0174861 A1 | 6/2016 | Cadwell | |

FOREIGN PATENT DOCUMENTS

| | | |
|---|---|---|
| EP | 972538 | 1/2000 |
| WO | 2000038574 A1 | 7/2000 |
| WO | 2000066217 A1 | 11/2000 |
| WO | 2001037728 A1 | 5/2001 |
| WO | 2003005887 A2 | 1/2003 |
| WO | 2005030318 A1 | 4/2005 |
| WO | 2006042241 A2 | 4/2006 |

OTHER PUBLICATIONS

"WinEEG: QEEG and ERP Analysis Software." Oct. 21, 2012. https://web.archive.org/web/20121021055030/http://www.mitsar-medical.com/eeg-software/geeg-software/.*

Panayiotopoulos, CP. "Chapter 10. Idiopathic Generalised Epilepsies." The Epilepsies: Seizures, Syndromes and Management. Oxfordshire (UK): Bladon Medical Publishing; 2005. 101 pages.*

Aage R. Møller, "Intraoperative Neurophysiologic Monitoring", University of Pittsburgh, School of Medicine Pennsylvania, © 1995 by Harwood Academic Publishers GmbH.

Clements, et. al., "Evoked and Spontaneous Electromyography to Evaluate Lumbosacral Pedicle Screw Placement", 21 (5):600-604 (1996).

Danesh-Clough, et. al., "The Use of Evoked EMG in Detecting Misplaced Thoracolumbar Pedicle Screws", 26(12):1313-1316 (2001).

Dezawa et al., "Retroperitoneal Laparoscopic Lateral Approach to the Lumbar Spine: A New Approach, Technique, and Clinical Trial", Journal of Spinal Disorders 13(2):138-143 (2000).

Dickman, et al., "Techniques in Neurosurgery", National Library of Medicine, 3 (4) 301-307 (1997).

Epstein, et al., "Evaluation of Intraoperative Somatosensory-Evoked Potential Monitoring During 100 Cervical Operations", 18(6):737-747 (1993), J.B. Lippincott Company.

Glassman, et. al., "A Prospective Analysis of Intraoperative Electromyographic Monitoring of Pedicle Screw Placement with Computed Tomographic Scan Confirmation", 20(12):1375-1379.

Goldstein, et. al., "Minimally Invasive Endoscopic Surgery of the Lumbar Spine", Operative Techniques in Orthopaedics, 7 (1):27-35 (1997).

Greenblatt, et. al., "Needle Nerve Stimulator-Locator", 41 (5):599-602 (1962).

H.M. Mayer, "Minimally Invasive Spine Surgery, A Surgical Manual", Chapter 12, pp. 117-131 (2000).

Hinrichs, et al., "A trend-detection algorithm for intraoperative ERH monitoring", Med. Eng. Phys. 18 (8):626-631 (1996).

Bergey et al., "Endoscopic Lateral Transpsoas Approach to the Lumbar Spine", SPINE 29 (15):1681-1688 (2004).

Holland, "Spine Update, Intraoperative Electromyography During Thoracolumbar Spinal Surgery", 23 (17):1915-1922 (1998).

Holland, et al., "Continuous Electromyographic Monitoring to Detect Nerve Root Injury During Thoracolumbar Scoliosis Surgery", 22 (21):2547-2550 (1997), Lippincott-Raven Publishers.

Hovey, A Guide to Motor Nerve Monitoring, pp. 1-31 Mar. 20, 1998, The Magstim Company Limited.

Kevin T. Foley, et. al., "Microendoscipic Discectomy" Techniques in Neurosurgery, 3:(4):301-307, © 1997 Lippincott-Raven Publishers, Philadelphia.

Kossmann et al., "The use of a retractor system (SynFrame) for open, minimal invasive reconstruction of the anterior column of the thoracic and lumbar spine", 10:396-402 (2001).

Kossmann, et. al., "Minimally Invasive Vertebral Replacement with Cages in Thoracic and Lumbar Spine", European Journal of Trauma, 2001, No. 6, pp. 292-300.

Lenke, et. al., "Triggered Electromyographic Threshold for Accuracy of Pedicle Screw Placement, An Animal Model and Clinical Correlation", 20 (14):1585-1591 (1995).

Lomanto et al., "7th World Congress of Endoscopic Surgery" Singapore, Jun. 1-4, 2000 Monduzzi Editore S.p. A.; email: monduzzi©monduzzi.com, pp. 97-103 and 105-111.

MaGuire, et. al., "Evaluation of Intrapedicular Screw Position Using Intraoperative Evoked Electromyography", 20 (9):1068-1074 (1995).

Mathews et al., "Laparoscopic Discectomy With Anterior Lumbar Interbody Fusion, A Preliminary Review", 20 (16):1797-1802, (1995), Lippincott-Raven Publishers.

Bertagnoli, et. al., "The AnteroLateral transPsoatic Approach (ALPA), A New Technique for Implanting Prosthetic Disc-Nucleus Devices", 16 (4):398-404 (2003).

Michael R. Isley, et. al., "Recent Advances in Intraoperative Neuromonitoring of Spinal Cord Function: Pedicle Screw Stimulation Techniques", Am. J. End Technol. 37:93-126 (1997).

Minahan, et. al., "The Effect of Neuromuscular Blockade on Pedicle Screw Stimulation Thresholds" 25(19):2526-2530 (2000).

Pimenta et. al., "Implante de prótese de núcleo pulposo: análise inicial", J Bras Neurocirurg 12 (2):93-96, (2001).

Raymond J. Gardocki, MD, "Tubular diskectomy minimizes collateral damage", AAOS Now, Sep. 2009 Issue, http://www.aaos.org/news/aaosnow/sep09/clinical12.asp.

Raymond, et. al., "The NerveSeeker: A System for Automated Nerve Localization", Regional Anesthesia 17:151-162 (1992).

Reidy, et. al., "Evaluation of electromyographic monitoring during insertion of thoracic pedicle screws", British Editorial Society of Bone and Joint Surgery 83 (7):1009-1014, (2001).

Rose et al., "Persistently Electrified Pedicle Stimulation Instruments in Spinal Instrumentation: Technique and Protocol Development", Spine: 22(3): 334-343 (1997).

Teresa Riordan "Patents; A businessman invents a device to give laparoscopic surgeons a better view of their worK", New York Times www.nytimes.com/2004/29/business/patents-businessman-invents-device-give-la (Mar. 2004).

Toleikis, et. al., "The usefulness of Electrical Stimulation for Assessing Pedicle Screw Placements", Journal of Spinal Disorders, 13 (4):283-289 (2000).

U.Schick, et. al., "Microendoscopic lumbar discectomy versus open surgery: an intraoperative EMG study", pp. 20-26, Published online: Jul. 31, 2001 © Springer-Verlag 2001.

Bose, et. al., "Neurophysiologic Monitoring of Spinal Nerve Root Function During Instrumented Posterior Lumbar Spine Surgery", 27 (13):1440-1450 (2002).

Vaccaro, et. al., "Principles and Practice of Spine Surgery", Mosby, Inc. © 2003, Chapter 21, pp. 275-281.

Vincent C. Traynelis, "Spinal arthroplasty", Neurosurg Focus 13 (2):1-7. Article 10, (2002).

Welch, et. al., "Evaluation with evoked and spontaneous electromyography during lumbar instrumentation: a prospective study", J Neurosurg 87:397-402, (1997).

Zouridakis, et. al., "A Concise Guide to Intraoperative Monitoring", Library of Congress card No. 00-046750, Chapter 3, p. 21, chapter 4, p. 58 and chapter 7 pp. 119-120.

Medtronic, "Nerve Integrity Monitor, Intraoperative EMG Monitor, User's Guide", Medtronic Xomed U.K. Ltd., Unit 5, West Point Row, Great Park Road, Almondsbury, Bristol B5324QG, England, pp. 1-39.

Chapter 9, "Root Finding and Nonlinear Sets of Equations", Chapter 9:350-354, http://www.nr.com.

Digitimer Ltd., 37 Hydeway, Welwyn Garden City, Hertfordshire. AL7 3BE England, email:sales@digitimer.com, website: www.digitimer.com, "Constant Current High Voltage Stimulator, Model DS7A, for Percutaneous Stimulation of Nerve and Muscle Tissue".

(56) References Cited

OTHER PUBLICATIONS

Ford et al, Electrical characteristics of peripheral nerve stimulators, implications for nerve localization, Dept. of Anesthesia, University of Cincinnati College of Medicine, Cincinnati, OH 45267, pp. 73-77.

Deletis et al, "The role of intraoperative neurophysiology in the protection or documentation of surgically induced injury to the spinal cord", Correspondence Address: Hyman Newman Institute for Neurology & Neurosurgery, Beth Israel Medical Center, 170 East End Ave., Room 311, NY 10128.

Urmey "Using the nerve stimulator for peripheral or plexus nerve blocks" Minerva Anesthesiology 2006; 72:467-71.

Butterworth et. al., "Effects of Halothane and Enflurane on Firing Threshold of Frog Myelinated Axon", Journal of Physiology 411:493-516, (1989) From the Anesthesia Research Labs, Brigham and Women's Hospital, Harvard Medical School, 75 Francis St., Boston, MA 02115, jp.physoc.org.

Calancie, et. al., "Threshold-level multipulse transcranial electrical stimulation of motor cortex for intraoperative monitoring of spinal motor tracts: description of method and comparison to somatosensory evoked potential monitoring" J Neurosurg 88:457-470 (1998).

Calancie, et. al., "Threshold-level repetitive transcranial electrical stimulation for intraoperative monitoring of central motor conduction", J. Neurosurg 95:161-168 (2001).

Calancie, et. al., Stimulus-Evoked EMG Monitoring During Transpedicular Lumbosacral Spine Instrumentation, Initial Clinical Results, 19 (24):2780-2786 (1994).

Carl T. Brighton, "Clinical Orthopaedics and Related Research", Clinical Orthopaedics and related research No. 384, pp. 82-100 (2001).

Office Action dated Oct. 16, 2017 for U.S. Appl. No. 14/206,945; (pp. 1-12).

Notice of Allowance dated Jun. 13, 2018 for U.S. Appl. No. 14/206,945 (pp. 1-12).

Notice of Allowability dated Jun. 25, 2018 for U.S. Appl. No. 14/206,945 (pp. 1-4).

Office Action dated Nov. 22, 2017 for U.S. Appl. No. 15/056,681; (pp. 1-5).

Notice of Allowanance dated Apr. 5, 2018 for U.S. Appl. No. 15/056,681 (pp. 1-5).

\* cited by examiner

2500

2502
Receive electroencephalography data comprising a plurality of EEG channels, wherein each EEG channel of the plurality of EEG channels comprises a plurality of EEG instances

2504
Receive video data of a subject from which the received EEG data is based

2506
Correlate each EEG instance of the plurality of EEG instances to a respective portion of the video data in a database

2508
Receive a first user input selecting a first EEG instance of the plurality of EEG instances

2510
In response to receiving the first user input, cross-reference the first EEG instance with the database to determine a first portion of the video data that corresponds to the first EEG instance

2512
Generate for display, on a display device, the first portion

| First Name | Last Name | Date Recorded | Location | Study Type | Record Status | Physician | Referring Physician |
|---|---|---|---|---|---|---|---|
| V52MCiud | v6f2SAxn | 1/17/2016 | Server | ICU EEG | Ready to Read | | |

Anonymize Records — 3100

3102 — First Name
3104 — Last Name
3106 — Date Recorded
3108 — Export

METHODS AND SYSTEMS FOR SIMULTANEOUS REVIEW OF BRAIN ACTIVITY AND PHYSICAL MANIFESTATIONS OF USERS

This application claims the benefit of U.S. Provisional Application No. 62/139,151, filed Mar. 27, 2015, which is hereby incorporated by reference herein in its entirety.

BACKGROUND

Electroencephalography ("EEG"), which involves recording electrical activity along the scalp, is a valuable tool in detecting and monitoring for a host of neurological disorders. For example, by comparing the recorded electrical activity (e.g., voltage fluctuations) in a brain of a subject to the physical manifestations (e.g., a seizure) observed in the subject, a practitioner may diagnosis the particular neurological disorder (e.g., epilepsy). However, even if EEG and video data is readily available, the practitioner still faces the hurdle of identifying what physical manifestations correspond to what electrical activity. This process is further complicated by the fact that in addition to observing a subject for the slightest physical manifestation (e.g., a movement of a finger, a blink of an eye, a twitch of a lip, etc.), the practitioner must simultaneously review numerous channels of incoming EEG data for millisecond fluctuations, any of which may affect an eventual diagnosis.

SUMMARY

Accordingly, methods and systems are disclosed herein for a guidance application that allows a practitioner to easily correlate a fluctuation in any channel of a plurality of channels constituting received electroencephalography ("EEG") data to a particular physical manifestation. For example, by improving the ability of a practitioner to correlate a millisecond fluctuation in a single channel of EEG data to even the slightest of physical manifestations, the likelihood that the practitioner can accurately diagnose a cause of an underlying neurological disorder is increased.

Specifically, the guidance application provides a series of user interfaces that allows a practitioner to simultaneously observe both incoming EEG data and physical manifestations of the subject. Furthermore, the guidance application automatically synchronizes incoming EEG data to the physical manifestations. For example, the guidance application allows a practitioner to automatically retrieve a portion of video data (e.g., of a physical manifestation of a subject) that corresponds to a selected portion of EEG data (e.g., of an electrical fluctuation of the brain activity of the subject). Moreover, the guidance application allows a practitioner to highlight and compare the selected portion to other selected portions in order to ease any review and analysis.

In some aspects, the guidance application may receive EEG data comprising a plurality of EEG channels, in which each EEG channel of the plurality of EEG channels comprises a plurality of EEG instances. For example, in order to monitor brain activity of a subject, the guidance application may receive EEG data from multiple electrodes attached to the scalp of the subject, in which each electrode corresponds to a particular channel. Furthermore, each channel may correspond to real-time voltage fluctuations in the brain activity of the user. The guidance application may also receive video data of a subject to which the multiple electrodes are attached. For example, in addition to monitoring brain activity of the user, the guidance application may monitor physical manifestations by generating a video recording of the subject.

The guidance application may correlate each EEG instance of the plurality of EEG instances to a respective portion of the video data in a database. For example, the guidance application may generate a time stamp for each EEG instance, each of which corresponds to a time stamp for a portion of the video data. The various time stamp may then be stored for later retrieval.

The guidance application may then receive a first user input selecting a first EEG instance of the plurality of EEG instances. For example, the guidance application may receive a user input selecting a particular EEG instance (e.g., corresponding to a large voltage fluctuation) for which a practitioner wishes to examine a subject for a corresponding physical manifestation.

In response to receiving the first user input, the guidance application may cross-reference the first EEG instance with the database to determine a first portion of the video data that corresponds to the first EEG instance. For example, the guidance application may determine the time stamp corresponding to the EEG instance and match that time stamp with a time stamp corresponding to a portion of the video data.

The guidance application may then generate for display, on a display device, the first portion. For example, in response to the request of the practitioner to view the physical manifestation of a large voltage fluctuation in the EEG data, the guidance application presents a portion of video data that corresponds to the large voltage fluctuation.

The guidance application may continue to generate for display the first portion until the end of the video data or until the guidance application receives a second user input (e.g., corresponding to a second EEG instance), at which point the first portion is replaced with a second portion of the video data (e.g., corresponding to second EEG instance). Accordingly, the guidance application may easily facilitate the review of physical manifestations corresponding to any voltage fluctuation (or lack thereof) in order to diagnosis a neurological disorder.

In some embodiments, the guidance application may generate for display a graphical representation of each EEG channel in a region of a display screen. The region may be divided into a plurality of sub-regions, in which each sub-region corresponds to a particular portion of the video data and/or EEG instances with a particular time stamp. Furthermore, the guidance application may be configured to allow a practitioner to select a particular EEG instance by hovering over the sub-region corresponding to the particular portion.

In some aspects, the guidance application may receive electroencephalography data comprising a plurality of EEG channels received from a subject during a hyperventilation period and post-hyperventilation period, in which each EEG channel of the plurality of EEG channels comprises a plurality of EEG instances. For example, in some cases, a practitioner may need to induce hyperventilation (e.g., a condition in which the brain of a subject is stressed) in order to diagnosis a neurological disorder. However, as such inductions involve safety concerns to the subject, the practitioner must actively monitor the incoming EEG data and the length of the hyperventilation of the subject.

To ensure patient safety, the guidance application may receive a first user input defining the hyperventilation period and a second user input defining the post-hyperventilation period. For example, the guidance application may receive an input from the practitioner indicating how long a user should remain in a hyperventilation state as well as how long a user needs to recover.

The guidance application may then correlate each EEG instance of the plurality of EEG instances received in incoming EEG data to a progression of the subject through the hyperventilation period and the post-hyperventilation period. For example, the guidance application may both receive and record incoming EEG data, but also manage the progression of the subject through the hyperventilation period and the post-hyperventilation period by generating for display, on a display screen, an on-screen graphic corresponding to the progression. For example, in order to allow the practitioner to analyze the incoming EEG without losing track of the length of the hyperventilation of the user, the guidance application may generate an on-screen graphic that intuitively informs the practitioner of the progress of the subject. For example, the on-screen graphic may include a first portion that corresponds to the hyperventilation period and a second portion that corresponds to the post-hyperventilation period.

In some embodiments, to increase the intuitiveness of the on-screen graphic and to reduce the reliance on textual elements (which may require a greater amount of the attention of the practitioner to monitor), the on-screen graphic may include one or more non-textual elements that indicate the progression of the subject through the hyperventilation period and the post-hyperventilation period. For example, the guidance application may determine whether the progression corresponds to a hyperventilation period or a post-hyperventilation period and modify the characteristics (e.g., size, shape, color, etc.) of the textual elements accordingly.

Finally, in some aspects, the guidance application may receive user inputs highlighting one or more portions of EEG data. For example, the user inputs may highlight portions of EEG data that include particular voltage fluctuations that a practitioner wishes to analyze in detail. In order to facilitate easy review of these portions, the guidance application may provide options for the practitioner to view truncated EEG data that features only the highlighted portions.

Furthermore, the guidance application may allow a practitioner to interactively adjust the EEG data that is truncated such that the practitioner can understand the relationship between highlighted EEG data and adjacent, unhighlighted EEG data. For example, the guidance application may provide options for incrementally increasing or decreasing the amount of EEG data that is truncated.

It should be noted, the embodiments described above may be applied to, or used in accordance with, other embodiments throughout this disclosure.

BRIEF DESCRIPTION OF THE DRAWINGS

The above and other objects and advantages of the disclosure will be apparent upon consideration of the following detailed description, taken in conjunction with the accompanying drawings, in which like reference characters refer to like parts throughout, and in which:

FIG. 25 shows a flowchart of illustrative steps for determining video data that corresponds to a selected EEG instance in accordance with some embodiments of the disclosure;

FIG. 31 shows an illustrative display screen indicating a window containing anonymized records of EEG data ready to be exported in accordance with some embodiments of the disclosure.

DETAILED DESCRIPTION

Figure 1:
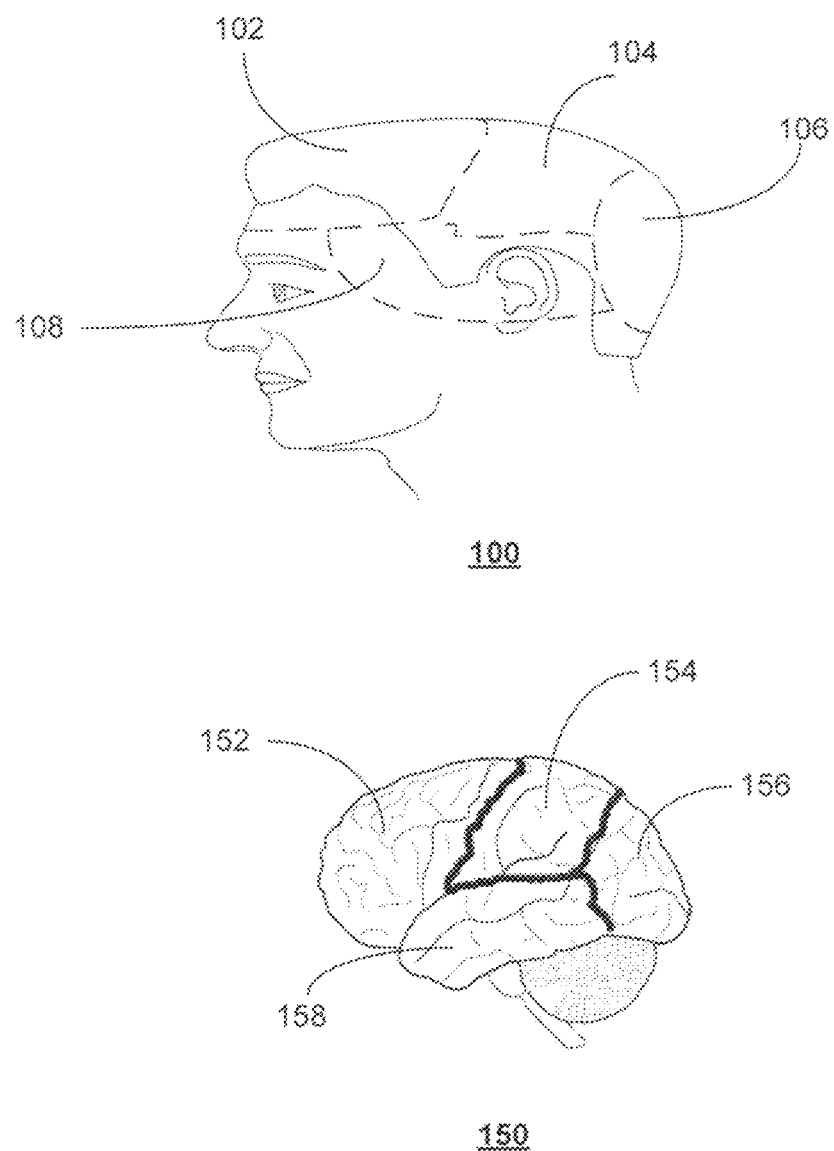
FIG. 1 is an illustrative diagram of a brain of a user in accordance with some embodiments of the disclosure.

Methods and systems are disclosed herein for a guidance application that allows a practitioner to easily correlate a fluctuation in any channel of a plurality of channels constituting received electroencephalography ("EEG") data to a particular physical manifestation. For example, by improving the ability of a practitioner to correlate a millisecond fluctuation in a single channel of EEG data to even the slightest of physical manifestations, the likelihood that the practitioner can accurately diagnose a cause of an underlying neurological disorder is increased.

As referred to herein, a "guidance application" is an application that facilitates the receipt, navigation, and/or viewing of EEG data. The guidance application and/or any instructions for performing any of the embodiments discussed herein may be encoded on computer readable media. Computer readable media includes any media capable of storing data. The computer readable media may be transitory, including, but not limited to, propagating electrical or electromagnetic signals, or may be non-transitory including, but not limited to, volatile and nonvolatile computer memory or storage devices such as a hard disk, floppy disk, USB drive, DVD, CD, media cards, register memory, processor caches, Random Access Memory ("RAM"), etc.

As referred to herein, "EEG data" is data received via electroencephalography. For example, EEG data may correspond to real-time voltage fluctuations in the brain activity of the user resulting from ionic current flows within the neurons of the brain. The guidance application may receive EEG data via a plurality of EEG channels. Each EEG channel may correspond to EEG data received from a specific EEG electrode. Furthermore, EEG data may include a plurality of EEG instances. As referred to herein, an "EEG instance" is EEG data that is received at a particular point in time. For example, EEG data may be received in a continuous or real-time manner as a practitioner performs an EEG test on a subject. While the test is being performed, the guidance application may receive a continuous stream of EEG data, which includes a series of EEG instances.

The guidance application may also monitor (e.g., via video recording) physical manifestations of a subject. As referred to herein, a "physical manifestation" is any event or action performed by a subject that may be observed through visual observation (e.g., a movement of a finger, a blink of an eye, a twitch of a lip, an uneven breathing pattern, any increase rate of perspiration, etc.). For example, in addition to monitoring brain activity of the user, the guidance application may monitor physical manifestations by generating a video recording of the user.

In some embodiments, the guidance application may receive electroencephalography data comprising a plurality of EEG channels received from a subject during a hyperventilation period and post-hyperventilation period, in which each EEG channel of the plurality of EEG channels comprises a plurality of EEG instances. As referred to herein, a "hyperventilation period" is a period of time associated with the hyperventilation (or the goal of inducing a hyperventilation) of a subject. As referred to herein, a "post-hyperventilation period" is a period of time that is not associated with the hyperventilation (or the goal of inducing a hyperventilation) of a subject.

To ensure patient safety, the guidance application may receive a first user input defining the hyperventilation period and a second user input defining the post-hyperventilation period. The guidance application may then generate for display, on a display screen, an on-screen graphic corresponding to the progression of a subject through the hyperventilation period and the post-hyperventilation period.

A referred to herein, an "on-screen graphic" is any human-consumable data that is visually displayed on a display screen. For example, an on-screen graphic may include any visual such as a drawing, a graph, a chart, an image, etc. The on-screen graphic may include both textual elements (e.g., number, letters, etc.) or non-textual elements (e.g., symbols, shapes, images, etc.). The elements of the on-screen graphic may include various characteristics (e.g., related to size, shape, brightness, hue, opaqueness, and/or any other feature or quality that may visually distinguish one element from another). In some embodiments, the guidance application may vary the characteristics of textual and non-textual elements in order to distinguish particular data or otherwise gain the attention of a practitioner. For example, a non-textual element associated with a hyperventilation period in an on-screen graphic may have one or more different characteristics than a non-textual element associated with a post-hyperventilation period in the on-screen graphic. Such variances are key in intuitively alerting a practitioner to changes in data or conditions.

FIG. 1 shows a representation of a user and regions of the brain of the user associated with monitoring brain activity. For example, in some embodiments, the guidance application may be implemented upon (or be in communication with) a user device that monitors brain activity of a user. The user device may reside upon the head of a user and include components (or sub-components) for testing different areas of the scalp of a user, or regions of the surface of a user's cranium.

For example, the scalp or cranium surface of user 100 includes first portion 102, second portion 104, third portion 106, and fourth portion 108. In some embodiments, each of first portion 102, second portion 104, third portion 106, and fourth portion 108 may correspond to a different region of brain 110. During EEG, a position on the scalp of a user (e.g., user 100) may correspond to a region of a brain (e.g., brain 150) of the user. For example, in some embodiments, first portion 102 may correspond to frontal lobe 112, second portion 104 may correspond to parietal lobe 114, third portion 106 may correspond to occipital lobe 116, and fourth portion 108 may correspond to temporal lobe 118. The voltage fluctuations associated with a specific region of the brain may provide evidence of specific neurological disorders. In addition, voltage fluctuations associated with a specific region of the brain may often correlate to specific physical manifestations.

Figure 2:
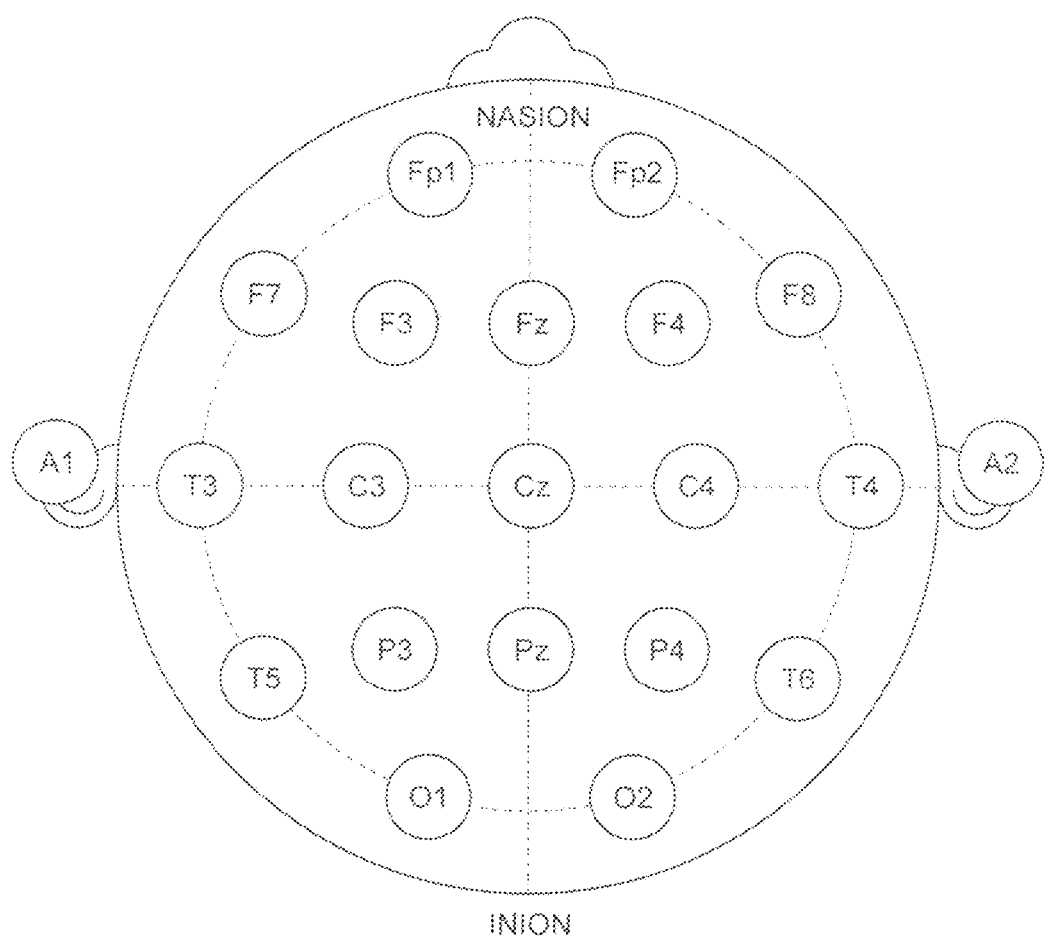
FIG. 2 is a top down diagram illustrating positions on a cranium where EEG electrodes may be placed to monitor brain activity of a user in accordance with some embodiments of the disclosure.

During an EEG test, a practitioner may distribute a plurality of electrodes about the scalp of a user in order to detect voltage fluctuations resulting from ionic current flows within the neurons of the various regions of the brain as shown in FIG. 2.

FIG. 2 is a top down diagram illustrating positions on a cranium where EEG electrodes may be placed to monitor brain activity of a user. The positions illustrated correspond to a subset of the 10-20 system. Each position is labeled by at least a letter and a numeric index. The letter corresponds to a portion of a scalp of a user (e.g., user 100 (FIG. 1)) and associated portion or region of a brain of the user (e.g., brain 150 (FIG. 1)). For example, "F" corresponds to the frontal lobe, "P" corresponds to the parietal lobe, "T" corresponds to the temporal lobe and "O" corresponds to the occipital lobe. "C" is used for identification purposes. The letter "z" indicates that an EEG electrode is positioned on the midline. In addition to the letter codes "F, P, O and C", the letter code "A" corresponds to the ear lobes, "Pg" corresponds to the nasopharyngeal lobe and "Fp" corresponds to the frontal polar position.

Each of the positions identified in FIG. 2 can detect brain activity from an associated lobe, brain portion, or brain region. For example, position F7 may detect brain signals from the frontal lobe while position O14 may detect brain signals from the occipital lobe. Accordingly, if a performance of a particular physical manifestation corresponds to the triggering of brain signals associated with a particular region of the brain (e.g., the frontal lobe), the guidance application may monitor EEG data received from that region of the brain for voltage fluctuations. The guidance application may then retrieve vide data corresponding to the brain signals, from which a practitioner may verify the occurrence of the physical manifestation in the subject.

Figure 3:
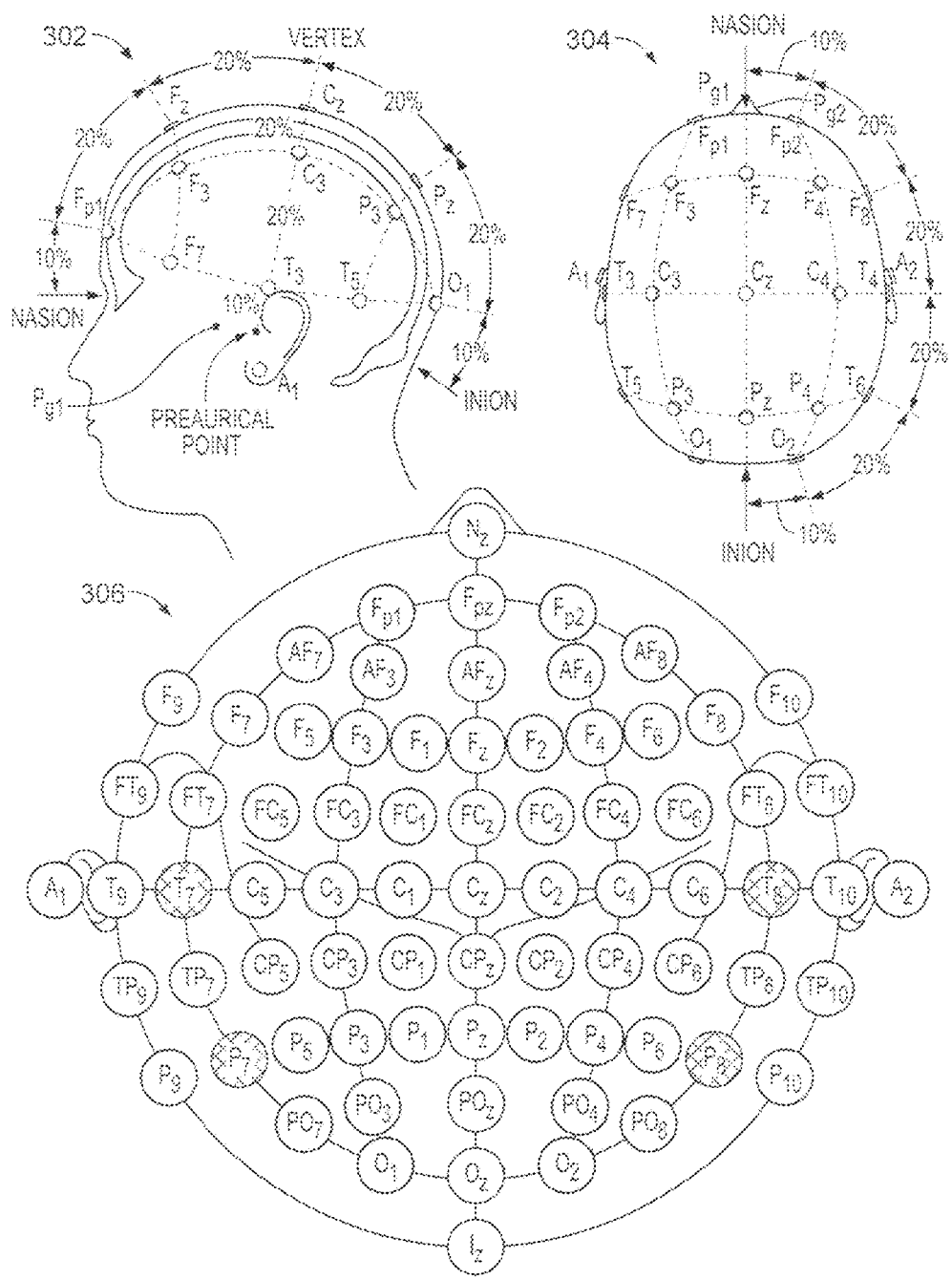
FIG. 3 shows detailed diagrams illustrating positions on a cranium where EEG electrodes may be placed to monitor brain activity of a user in accordance with some embodiments of the disclosure.

FIG. 3 shows detailed diagrams illustrating positions on a cranium where brain activity detectors may be placed to monitor brain activity of a user. Diagram 302 illustrates a side view of a cranium of a subject and corresponding positions for placement of EEG electrodes. Diagram 304 illustrates a top view of a cranium of a subject and corresponding positions for placement of EEG electrodes. Diagram 306 illustrates and labels "10%" positions as standardized by the American Electroencephalographic Society. The "10%" positions correspond to spacings of 10% of the total distance across an arc that traverses the outer surface of the cranium. These standardized positions provide common reference points for detecting information for corresponding brain regions. For example, position T3 corresponds to the temporal lobe located above the ear, and may correspond to hearing functions. EEG electrodes positioned at T3 would measure brain signals indicative of hearing activity.

The positions labeled and identified in FIG. 2 and FIG. 3 may correspond to positions for placement of EEG electrodes, and accordingly, placement of any of user equipment device (e.g., user equipment device 400 (FIG. 4)) configured to monitor EEG data. A user device configured to monitor EEG data and upon which a guidance application may be implemented is discussed in FIG. 4.

Figure 4:
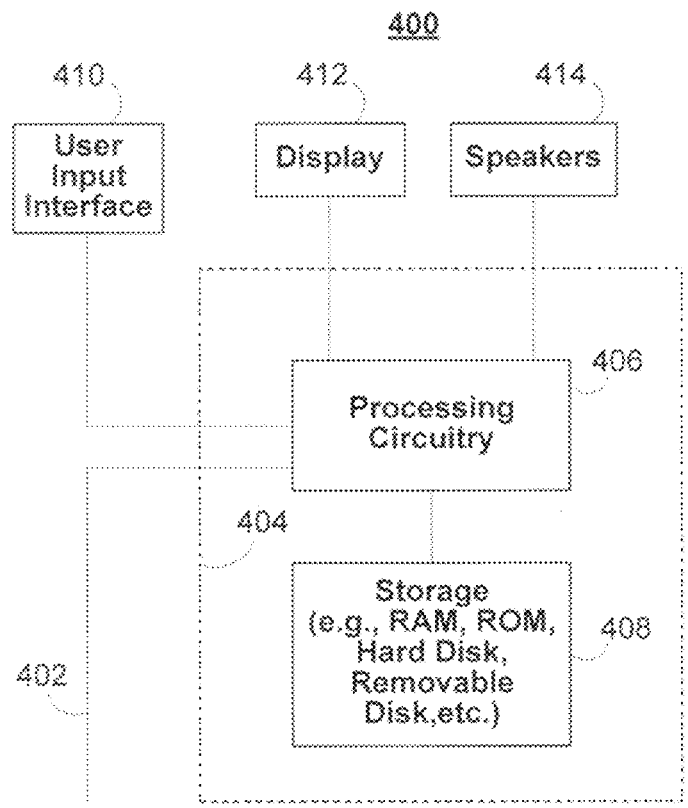
FIG. 4 is a block diagram of an illustrative system upon which a guidance application may be implemented in accordance with some embodiments of the disclosure.

FIG. 4 shows a generalized embodiment of illustrative user equipment device 400. User equipment device 400 may receive EEG data, which may include a plurality of EEG channels, and of which each EEG channel of the plurality of EEG channels comprises a plurality of EEG instances, via input/output (hereinafter "I/O") path 402. For example, I/O path 402 may include one or more EEG electrodes (which are not shown for simplicity).

Control circuitry 404 may be based on any suitable processing circuitry such as processing circuitry 406. As referred to herein, processing circuitry should be understood to mean circuitry based on one or more microprocessors, microcontrollers, digital signal processors, programmable logic devices, field-programmable gate arrays (FPGAs), application-specific integrated circuits (ASICs), etc., and may include a multi-core processor (e.g., dual-core, quad-core, hexa-core, or any suitable number of cores) or supercomputer. In some embodiments, processing circuitry may be distributed across multiple separate processors or processing units, for example, multiples of the same type of processing units (e.g., two Intel Core i7 processors) or multiple different processors (e.g., an Intel Core i5 processor and an Intel Core i7 processor). In some embodiments, control circuitry 404 executes instructions for a guidance application stored in memory (i.e., storage 408). Specifically, control circuitry 404 may be instructed by the guidance application to perform the functions discussed above and below. For example, the guidance application may provide instructions to control circuitry 404 to monitor and record EEG data and/or execute user inputs. In some implementations, any action performed by control circuitry 404 may be based on instructions received from the guidance application.

In client-server based embodiments, control circuitry 404 may include communications circuitry suitable for communicating with a guidance application server or other networks or servers. The instructions for carrying out the above mentioned functionality may be stored on the guidance application server. Communications circuitry may include a cable modem, an integrated services digital network (ISDN) modem, a digital subscriber line (DSL) modem, a telephone modem, Ethernet card, or a wireless modem for communications with other equipment, or any other suitable communications circuitry. Such communications may involve the Internet or any other suitable communications networks or paths. In addition, communications circuitry may include circuitry that enables peer-to-peer communication of user equipment devices, or communication of user equipment devices in locations remote from each other (described in more detail below).

Memory may be an electronic storage device provided as storage 408 that is part of control circuitry 404. As referred to herein, the phrase "electronic storage device" or "storage device" should be understood to mean any device for storing electronic data, computer software, or firmware, such as random-access memory, read-only memory, hard drives, optical drives, digital video disc (DVD) recorders, compact disc (CD) recorders, BLU-RAY disc (BD) recorders, BLU-RAY 3D disc recorders, digital video recorders (DVR, sometimes called a personal video recorder, or PVR), solid state devices, quantum storage devices, gaming consoles, gaming media, or any other suitable fixed or removable storage devices, and/or any combination of the same. Storage 408 may be used to store various types of content described herein as well as media guidance data described above. Nonvolatile memory may also be used (e.g., to launch a boot-up routine and other instructions). Cloud-based storage may be used to supplement storage 408 or instead of storage 408.

Control circuitry 404 may include video generating circuitry and tuning circuitry, such as one or more analog tuners, one or more MPEG-2 decoders or other digital decoding circuitry, high-definition tuners, or any other suitable tuning or video circuits or combinations of such circuits. Encoding circuitry (e.g., for converting over-the-air, analog, or digital signals to MPEG signals for storage) may also be provided. Control circuitry 404 may also include scaler circuitry for upconverting and downconverting content into the preferred output format of the user equipment 400. Circuitry 404 may also include digital-to-analog converter circuitry and analog-to-digital converter circuitry for converting between digital and analog signals. The tuning and encoding circuitry may be used by the user equipment device to receive and to display, to play, or to record content.

A user may send instructions to control circuitry 404 using user input interface 410. User input interface 410 may be any suitable user interface, such as a remote control, mouse, trackball, keypad, keyboard, touch screen, touchpad, stylus input, joystick, voice recognition interface, or other user input interfaces. Display 412 may be provided as a stand-alone device or integrated with other elements of user equipment device 400. For example, display 412 may be a touchscreen or touch-sensitive display. In such circumstances, user input interface 410 may be integrated with or combined with display 412. Display 412 may be one or more of a monitor, a television, a liquid crystal display (LCD) for a mobile device, amorphous silicon display, low temperature poly silicon display, electronic ink display, electrophoretic display, active matrix display, electro-wetting display, electrofluidic display, cathode ray tube display, light-emitting diode display, electroluminescent display, plasma display panel, high-performance addressing display, thin-film transistor display, organic light-emitting diode display, surface-conduction electron-emitter display (SED), laser television, carbon nanotubes, quantum dot display, interferometric modulator display, or any other suitable equipment for displaying visual images. In some embodiments, display 412 may be HDTV-capable. In some embodiments, display 412 may be a 3D display, and the guidance application and any suitable content may be displayed in 3D. A video card or graphics card may generate the output to the display 412. The video card may offer various functions such as accelerated rendering of 3D scenes and 2D graphics, MPEG-2/MPEG-4 decoding, TV output, or the ability to connect multiple monitors. The video card may be any processing circuitry described above in relation to control circuitry 404. The video card may be integrated with the control circuitry 404. Speakers 414 may be provided as integrated with other elements of user equipment device 400 or may be stand-alone units. The audio component of videos and other content displayed on display 412 may be played through speakers 414. In some embodiments, the audio may be distributed to a receiver (not shown), which processes and outputs the audio via speakers 414.

The guidance application may be implemented using any suitable architecture. For example, it may be a stand-alone application wholly-implemented on user equipment device 400. In such an approach, instructions of the application are stored locally (e.g., in storage 408), and data for use by the application is downloaded on a periodic basis (e.g., from an out-of-band feed, from an Internet resource, or using another suitable approach). Control circuitry 404 may retrieve instructions of the application from storage 408 and process the instructions to generate any of the displays discussed herein. Based on the processed instructions, control circuitry 404 may determine what action to perform when input is received from user input interface 410. For example, movement of a cursor on a display up/down may be indicated by the processed instructions when input interface 410 indicates that an up/down button was selected.

In some embodiments, the guidance application is a client-server based application. Data for use by a thick or thin client implemented on user equipment device 400 is retrieved on-demand by issuing requests to a server remote to the user equipment device 400. In one example of a client-server based guidance application, control circuitry 404 runs a web browser that interprets web pages provided by a remote server. For example, the remote server may store the instructions for the application in a storage device. The remote server may process the stored instructions using circuitry (e.g., control circuitry 404) and generate the displays discussed above and below. The client device may receive the displays generated by the remote server and may display the content of the displays locally on equipment device 400. This way, the processing of the instructions is performed remotely by the server while the resulting displays are provided locally on equipment device 400. Equipment device 400 may receive inputs from the user via input interface 410 and transmit those inputs to the remote server for processing and generating the corresponding displays. For example, equipment device 400 may transmit a communication to the remote server indicating that an up/down button was selected via user input interface 410. The remote server may process instructions in accordance with that input and generate a display of the application corresponding to the input (e.g., a display that moves a cursor up/down). The generated display is then transmitted to equipment device 400 for presentation to the user.

In some embodiments, the guidance application is downloaded and interpreted or otherwise run by an interpreter or virtual machine (run by control circuitry 404). In some embodiments, the guidance application may be encoded in the ETV Binary Interchange Format (EBIF), received by control circuitry 404 as part of a suitable feed, and interpreted by a user agent running on control circuitry 404. For example, the guidance application may be an EBIF application. In some embodiments, the guidance application may be defined by a series of JAVA-based files that are received and run by a local virtual machine or other suitable middleware executed by control circuitry 404. In some of such embodiments (e.g., those employing MPEG-2 or other digital media encoding schemes), the guidance application may be, for example, encoded and transmitted in an MPEG-2 object carousel with the MPEG audio and video packets of a program.

Figure 5:
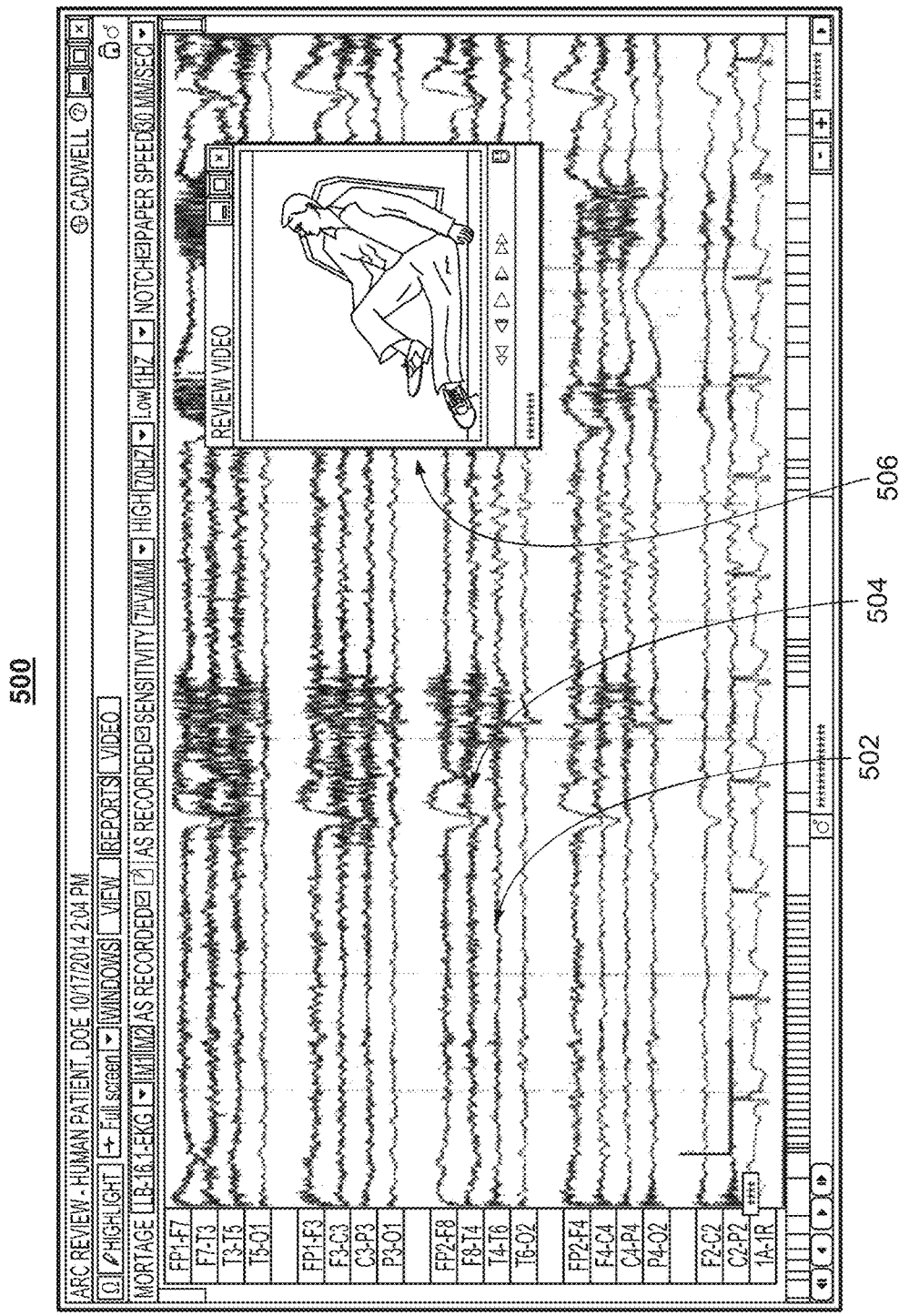
FIG. 5 shows an illustrative display screen featuring a first region that includes EEG data corresponding to a plurality of EEG channels and a second region that includes video data in accordance with some embodiments of the disclosure.

FIG. 5 shows an illustrative display screen (e.g., display 412 (FIG. 4)) featuring a first region that includes EEG data corresponding to a plurality of EEG channels and a second region that includes video data. First region 500 includes a plurality of EEG channels in a graphical representation. For example, in first region 500, the plurality of EEG channels are organized in a vertical manner along a first axis. EEG instances associated with each EEG channel extend horizontally along an axis perpendicular to the first axis. In some embodiments, each of the EEG channels is associated with a particular EEG electrode (e.g., as discussed above in FIGS. 2-3). For example, channel 502 corresponds to "T4-T6," whereas channel 054 corresponds to "F8-T4."

In addition to first region 500, FIG. 5 also includes a second region (e.g., video region 506). Video region 506 presents a video image of a subject from which the EEG data is generated. For example, as first region 500 shows EEG data as the EEG data is received from subject, video region 506 shows physical manifestations of a subject as the physical manifestations occur.

Figure 6:
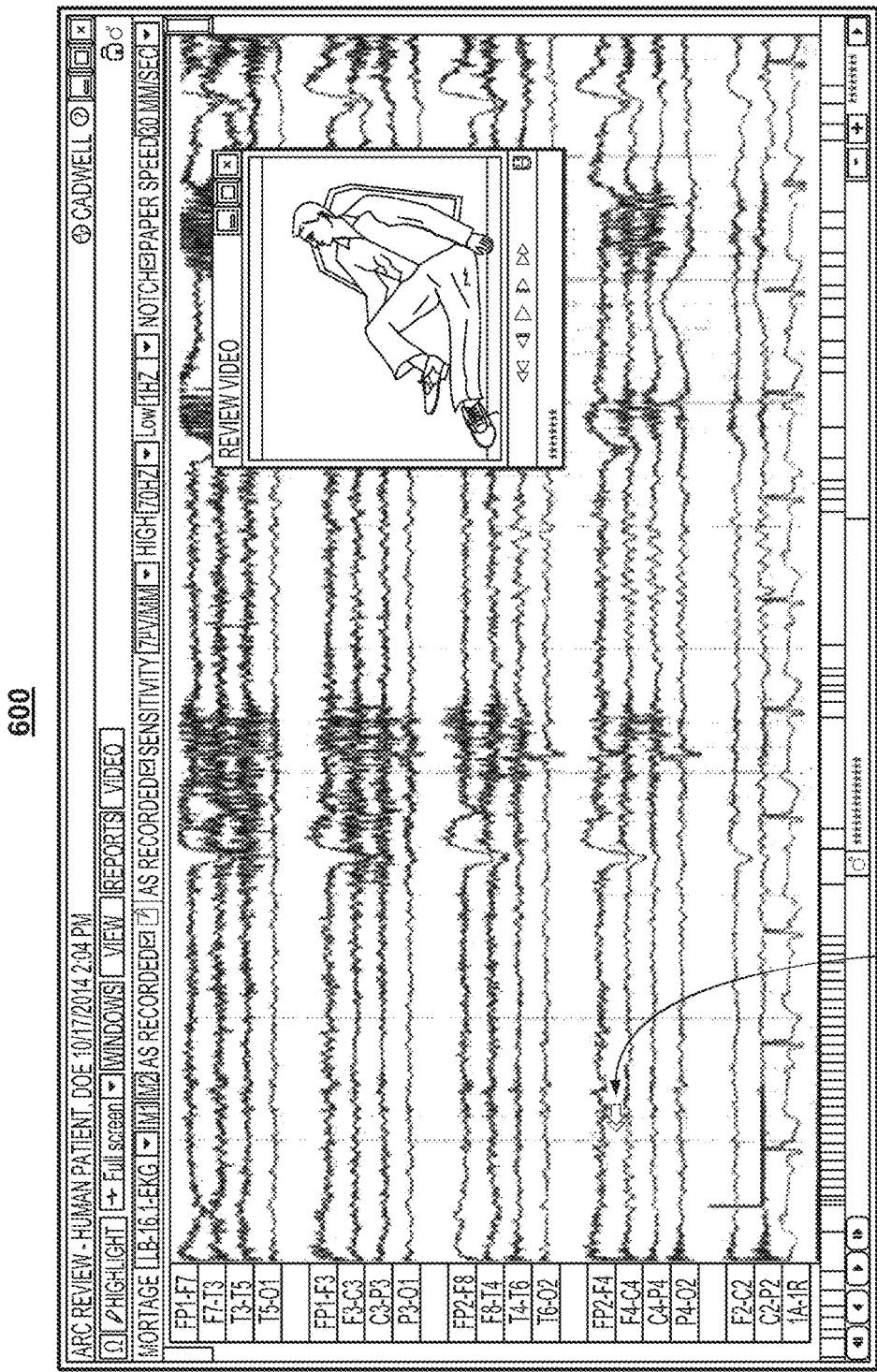
FIG. 6 shows an illustrative display screen in which video data shown in a second region corresponds to a location of an on-screen cursor in a first region in accordance with some embodiments of the disclosure.
Figure 7:
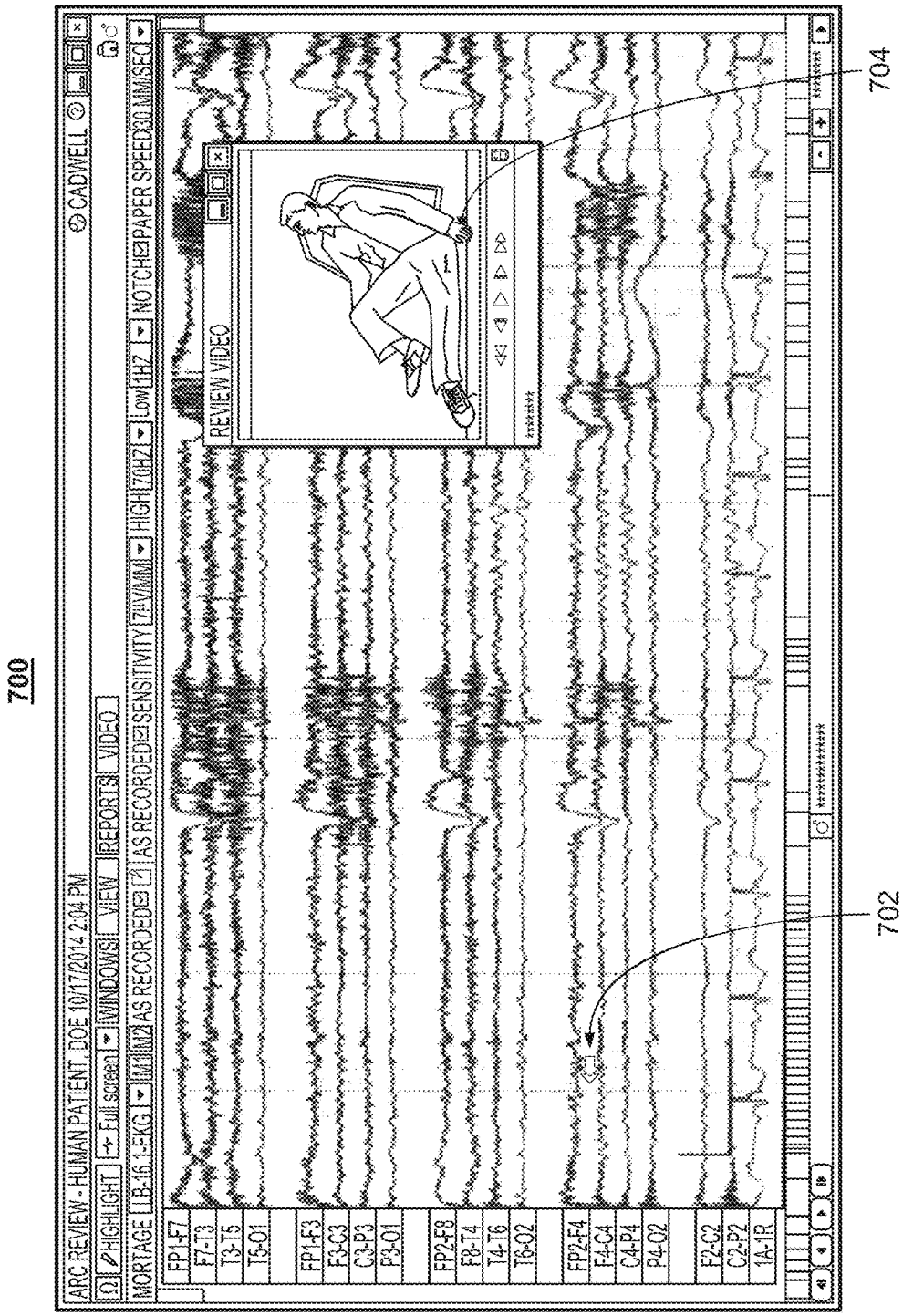
FIG. 7 shows an illustrative display screen in which displayed physical manifestations of a subject in a second region correspond to EEG data selected in a first region in accordance with some embodiments of the disclosure.
Figure 8:
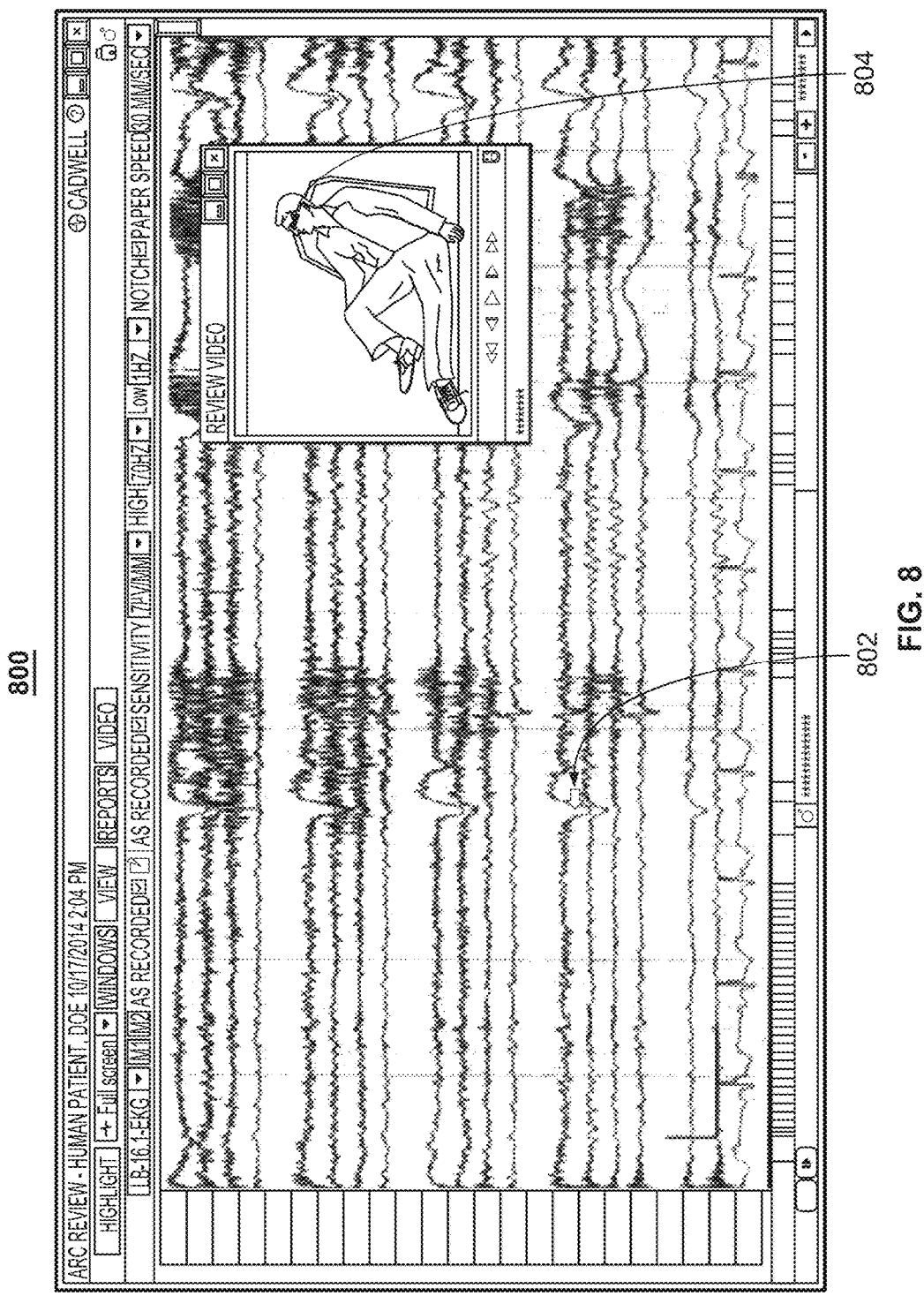
FIG. 8 shows another illustrative display screen in which displayed physical manifestations of a subject in a second region correspond to EEG data selected in a first region in accordance with some embodiments of the disclosure.

FIGS. 6-8 show illustrative display screens (e.g., display 412 (FIG. 4)) in which video data shown in a second region corresponds to a location of an on-screen cursor in a first region. For example, in first region 600 of FIG. 6, on-screen cursor 602 is hovering (e.g., in response to a user input entered via user input interface 410 (FIG. 4)) at a first sub-region. In response, the guidance application is presenting video data in a second region that corresponds to the EEG instance in the first sub-region. As on-screen cursor 602 is navigated (e.g., via a user input interface 410 (FIG. 4)) about first region 600, the portion of the video data generated for display in the second region changes.

For example, in FIG. 7, a location of on-screen cursor 702 in first region 700 corresponds to a different location than on-screen cursor 602 (FIG. 6)). For example, on-screen cursor 702 may correspond to a different sub-region of EEG than the sub-region of on-screen cursor 602 (FIG. 6)). For example, in response to receiving a user input (e.g., received via user input interface 40 (FIG. 4)), the guidance application may cross-reference (e.g., via control circuitry 404 (FIG. 4)) a sub-region associated with the user input (e.g., a sub-region over which an on-screen cursor hovers) with a database that lists portions of video data associated with each sub-region to determine a portion of video data that corresponds to the sub-region. The guidance application may then generate for display the determined portion of video data in a second region. For example, the video region in FIG. 7 includes physical manifestation 704, which corresponds to the twitch of a finger of the subject. This portion of video data corresponds to the sub-region over which on-screen cursor 702 hovers.

FIG. 8 shows another illustrative display screen (e.g., display 412 (FIG. 4)) in which displayed physical manifestations of a subject in a second region corresponds to EEG data selected in a first region. For example, in FIG. 8, the location of on-screen cursor 802 in first region 800 corresponds to a different location than on-screen cursor 702 (FIG. 7)). For example, the guidance application may have received a user input (e.g., via user input interface 410 (FIG. 4)) modifying the location of on-screen cursor 802. Alternatively or additionally, the guidance application may have automatically moved the location of on-screen cursor 802 in response to generating for display video data in a second region.

For example, after on-screen cursor 802 is positioned at a location in a first region (e.g., corresponding to a particular sub-region as discussed above), the guidance application may (e.g., via control circuitry 404 (FIG. 4)) generate for display a frame of the video data that corresponds to the position. Subsequently, the guidance application may receive a user input (e.g., via user input interface 410 (FIG. 4)) requesting that the video data begin playback from that frame. As the video data is played back, the EEG data in the first region begins to scroll such that the EEG data corresponding to the position of on-screen cursor 802 continues to correspond to the video data generated for display in the second region. Likewise, in response to other playback operations (e.g., rewinds, fast-forwards, skips, etc.), the guidance application may adjust (e.g., via control circuitry 404 (FIG. 4)) the location of an on-screen cursor in the EEG data in order to maintain the corresponds between the position of the on-screen cursor and the portion of the video data that is generated for display.

Figure 9:
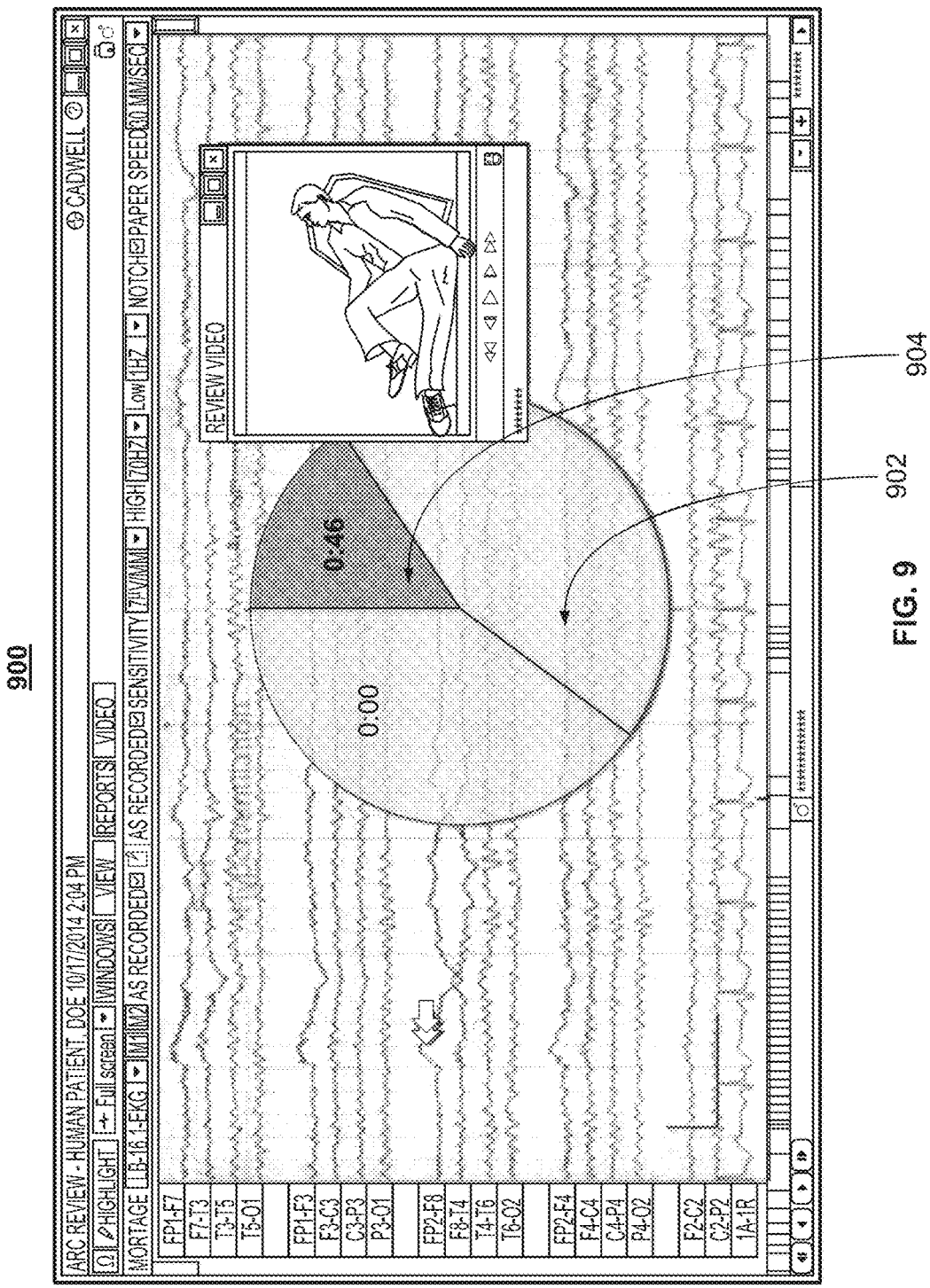
FIG. 9 shows an illustrative display screen featuring a first region featuring EEG data, a second region featuring video data, and an on-screen graphic indicating a progression of the subject through the hyperventilation period and the post-hyperventilation period in accordance with some embodiments of the disclosure.

FIG. 9 shows an illustrative display screen featuring first region 900 (e.g., featuring EEG data in a graphical representation) and a second region (e.g., featuring video data), and an on-screen graphic (e.g., indicating a progression of the subject through the hyperventilation period and the post-hyperventilation period) overlaid on first region 900. For example, in addition to first region 900 and the second region discussed in FIGS. 6-8, the guidance application has (e.g., via control circuitry 404 (FIG. 4)) additionally generated for display on-screen graphic 902. On-screen graphic 902 includes non-textual element 904 (e.g., a portion of the on-screen graphic that is shaded to indicate the progression of a subject through a hyperventilation period).

Figure 10:
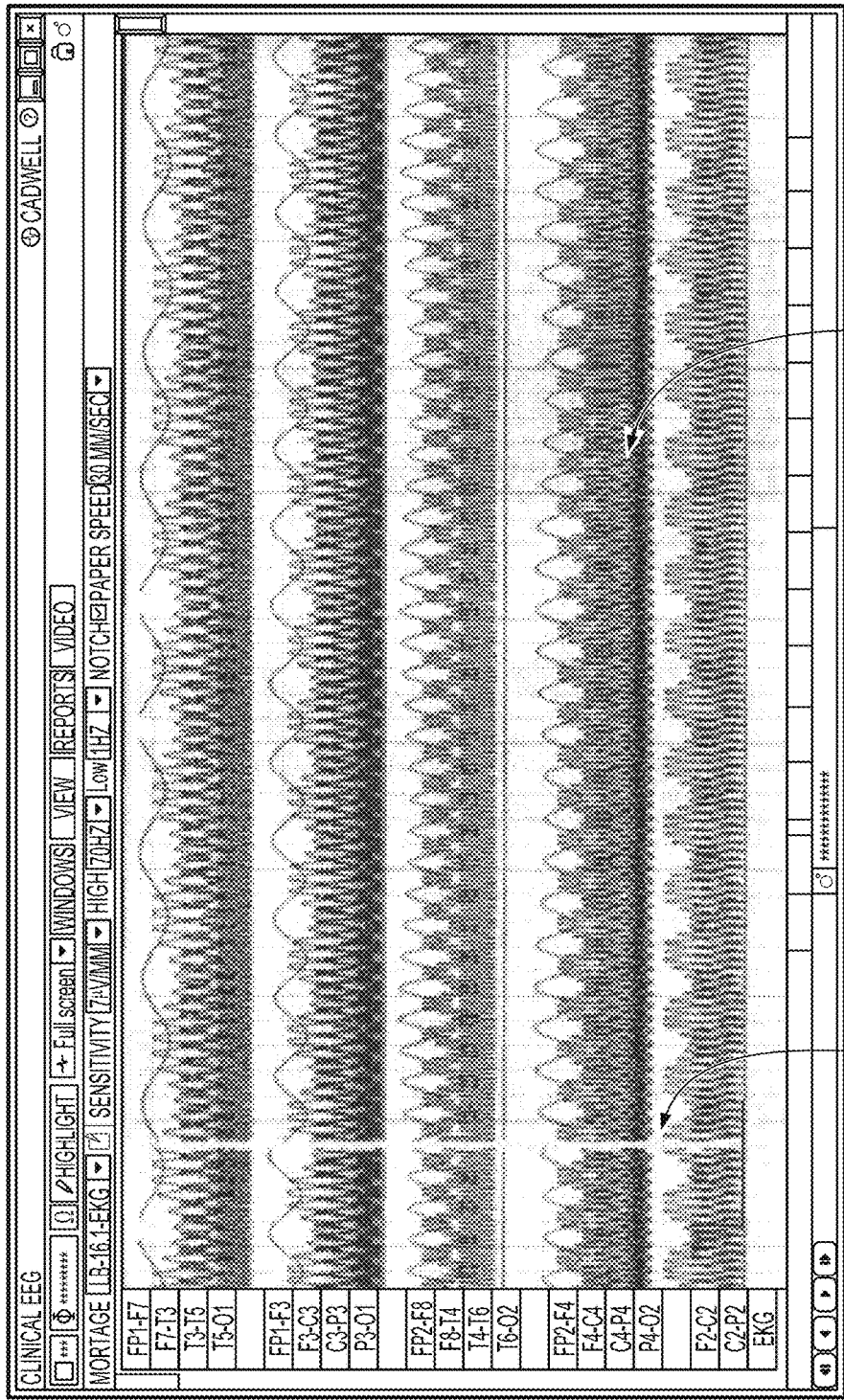
FIG. 10 shows an illustrative display screen in which received EEG data is generated for display in a graphical representation in accordance with some embodiments of the disclosure.

FIG. 10 shows an illustrative display screen (e.g., display 412 (FIG. 4)) on which received EEG data is generated for display in a graphical representation. The graphical representation of received EEG data may be used to correlate EEG data with video data, on-screen graphics, etc. For example, a graphical representation may occupy a first region (e.g., region 1000) of a display screen. The graphical representation may organize EEG data received by the guidance application into a plurality of EEG channels. As discussed above, each of the EEG channels may correspond to a different EEG electrode. Furthermore, the region featuring the graphical representation may feature a plurality of sub-regions. In some embodiments, the plurality of sub-regions may comprise a column that extends the height of the graphical representation in the vertical direction and includes only a single EEG instance in the horizontal direction. For example, the sub-region may include all EEG instances corresponding to a specific time across the plurality of EEG channels. In such cases, the guidance application may define a sub-region in terms of only coordinate along a horizontal axis (as opposed to defining the sub-region in terms of coordinate along both the horizontal and vertical axis).

The guidance application may (e.g., via control circuitry 404 (FIG. 4)) monitor the location of an on-screen cursor (e.g., on-screen cursor 602 (FIG. 6)) as the on-screen cursor is moved about the graphical representation. Furthermore, as the on-screen cursor is moved about the graphical representation, the guidance application may (e.g., via control circuitry 404 (FIG. 4)) continually determine which sub-region of the plurality of sub-regions corresponds to the current location of the on-screen cursor. For example, the guidance application may determine coordinates of the location of an on-screen cursor (e.g., x, y coordinates). The guidance application may then cross-reference the coordinates with a database that indicates the sub-region associated with different coordinates to determine a particular sub-region associated with the coordinates. The guidance application may then cross-reference the sub-region with a database that indicates a portion of video data, an on-screen graphic, etc.

associated with different sub-regions to determine a particular portion of video data, in-screen graphic, etc. associated with the sub-region.

Furthermore, in some embodiments, the guidance application may cross-reference a coordinate and/or a time stamp associated with the position of an on-screen cursor (or EEG data that corresponds to the position of the on-screen cursor) with a database that indicates a portion of video data, an on-screen graphic, etc. associated with different coordinates and/or a time stamps. For example, the guidance application may (e.g., via control circuitry 404 (FIG. 4)) user multiple techniques to determine what portion of vide data should be generated for display.

Figure 11:
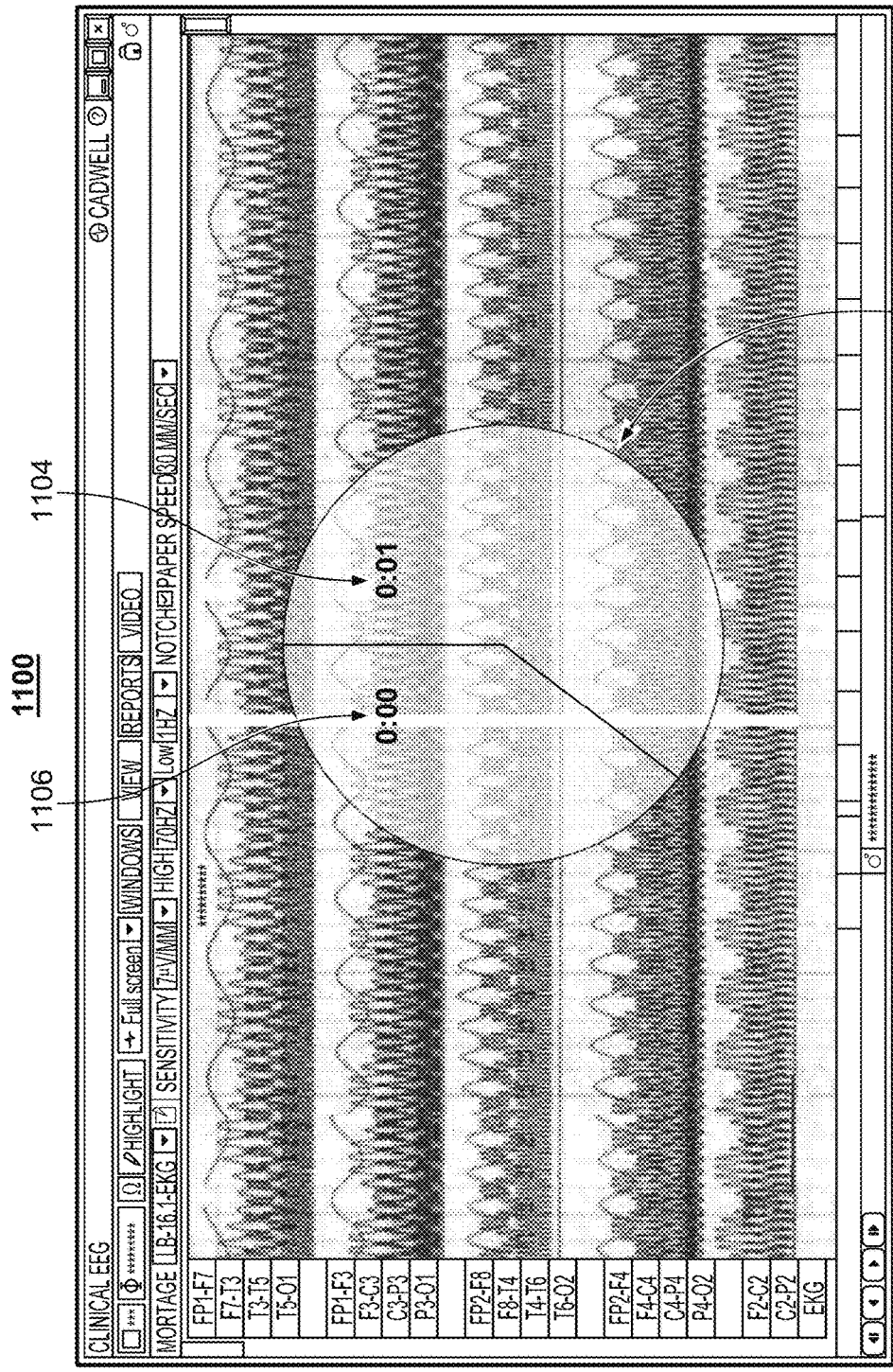
FIG. 11 shows an illustrative on-screen graphic indicating a progression of a subject through a hyperventilation period in accordance with some embodiments of the disclosure.

FIG. 11 shows an illustrative on-screen graphic (e.g., generated for display on display 412 (FIG. 4)) indicating a progression of a subject through a hyperventilation period. For example, on-screen graphic 1102 appears as a pie chart featuring first region 1104 (e.g., corresponding to a hyperventilation period) and second region 1106 (e.g., corresponding to a post-hyperventilation period). The amount of time corresponding to either region may depend on an amount of time selected for the hyperventilation period and the post-hyperventilation period.

For example, in order to intuitively present how much time remains in a hyperventilation or post-hyperventilation period, the guidance application (e.g., via control circuitry 404 (FIG. 4)) may gradually fill (or color) an on-screen graphic. For example, in the case of a pie chart on-screen chart, each second of progress may cause the guidance application to add an additional slice of the pie. Furthermore, the guidance application may gradually fill the on-screen graphic in a clockwise manner, which may be especially intuitive to a practitioner.

In some embodiments, the guidance application may receive (e.g., via control circuitry 404 (FIG. 4)) the amount of time selected for the hyperventilation period and the post-hyperventilation period from a practitioner (e.g., via user input interface 410 (FIG. 4)). Alternatively or additionally, the guidance application may (e.g., via control circuitry 404 (FIG. 4)) assign default periods of time that correspond to industry standards or periods specific to a particular subject (e.g., retrieved from storage 408 (FIG. 4)).

Figure 12:
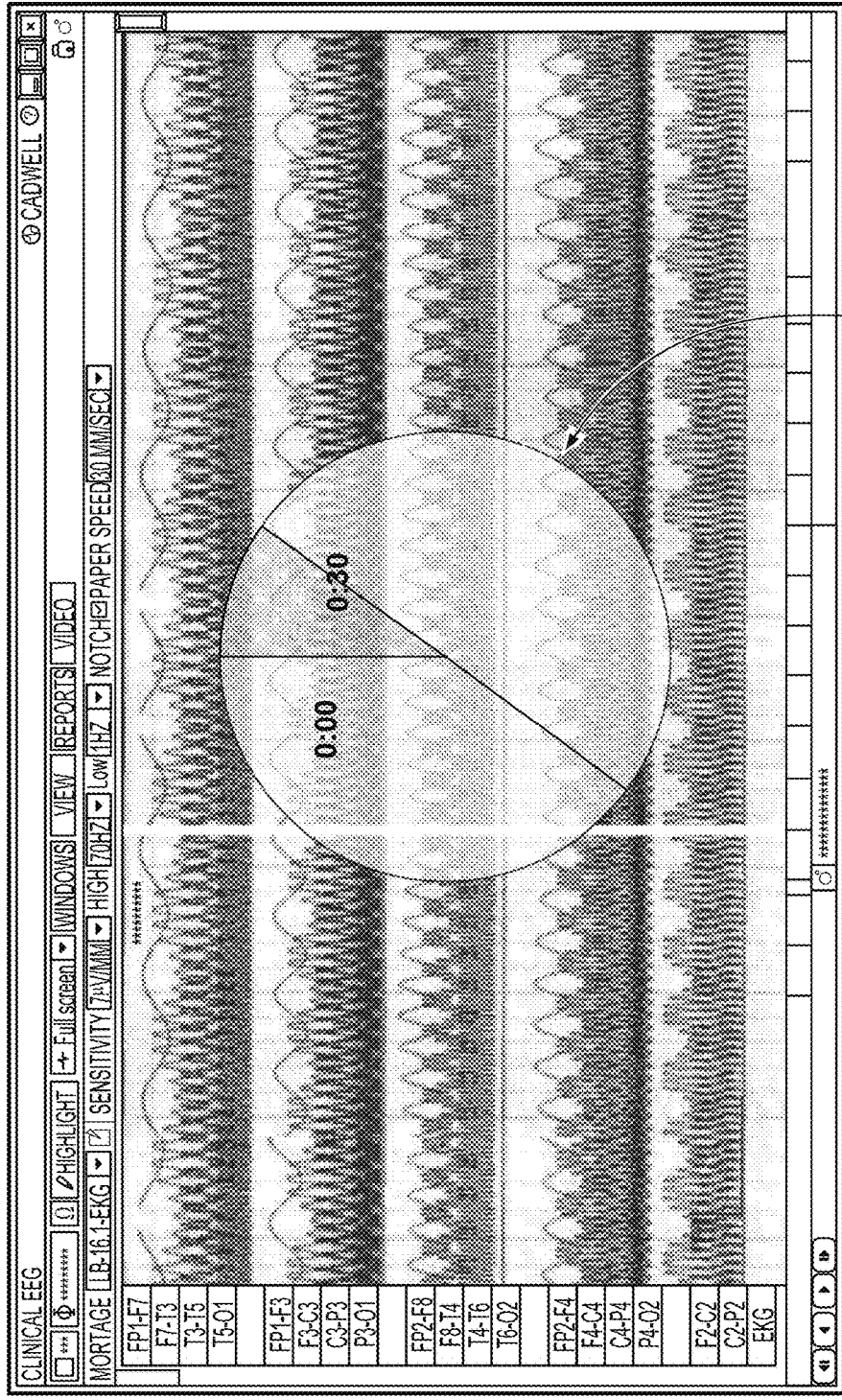
FIG. 12 shows an illustrative on-screen graphic indicating a progression of a subject through a hyperventilation period in accordance with some embodiments of the disclosure.

FIG. 12 shows an illustrative on-screen graphic (e.g., generated for display on display 412 (FIG. 4)) indicating a progression of a subject through a hyperventilation period. For example, on-screen graphic 1202, configured as a transparent overlay on region 1200, currently shows that a subject has progressed thirty seconds in a hyperventilation period. Accordingly, the guidance application has (e.g., via control circuitry 404 (FIG. 4)) modified a non-textual element of on-screen graphic 1202 to indicate the progress. For example, the guidance application has colored (e.g., via control circuitry 404 (FIG. 4)) a portion of on-screen graphic 1202 that corresponds to thirty seconds of progress in the hyperventilation period to intuitively indicate to a practitioner the progress of the subject.

Figure 13:
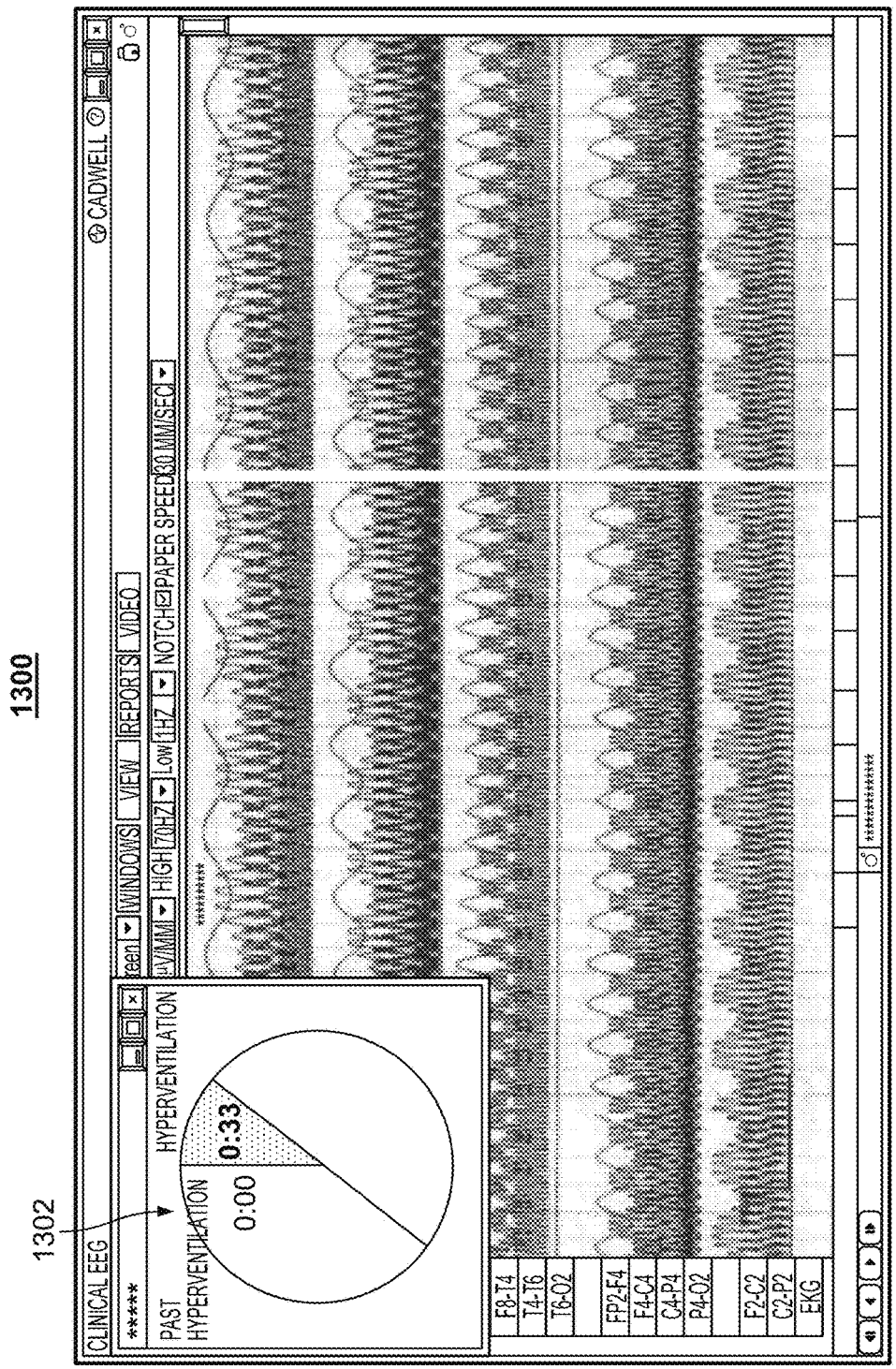
FIG. 13 shows another illustrative on-screen graphic indicating a progression of a subject through a hyperventilation period in accordance with some embodiments of the disclosure.

FIG. 13 shows another illustrative on-screen graphic (e.g., generated for display on display 412 (FIG. 4)) indicating a progression of a subject through a hyperventilation period. For example, in FIG. 13, the guidance application (e.g., via control circuitry 404 (FIG. 4)) generates on-screen graphic 1302 as a picture-in-a-picture ("PIP") window. For example, in response to a user input (e.g., received via user input interface 410 (FIG. 4)), the guidance application may change on-screen graphic 1302 from a transparent overlay (e.g., as shown in FIG. 12) to a PIP window overlay.

Figure 14:
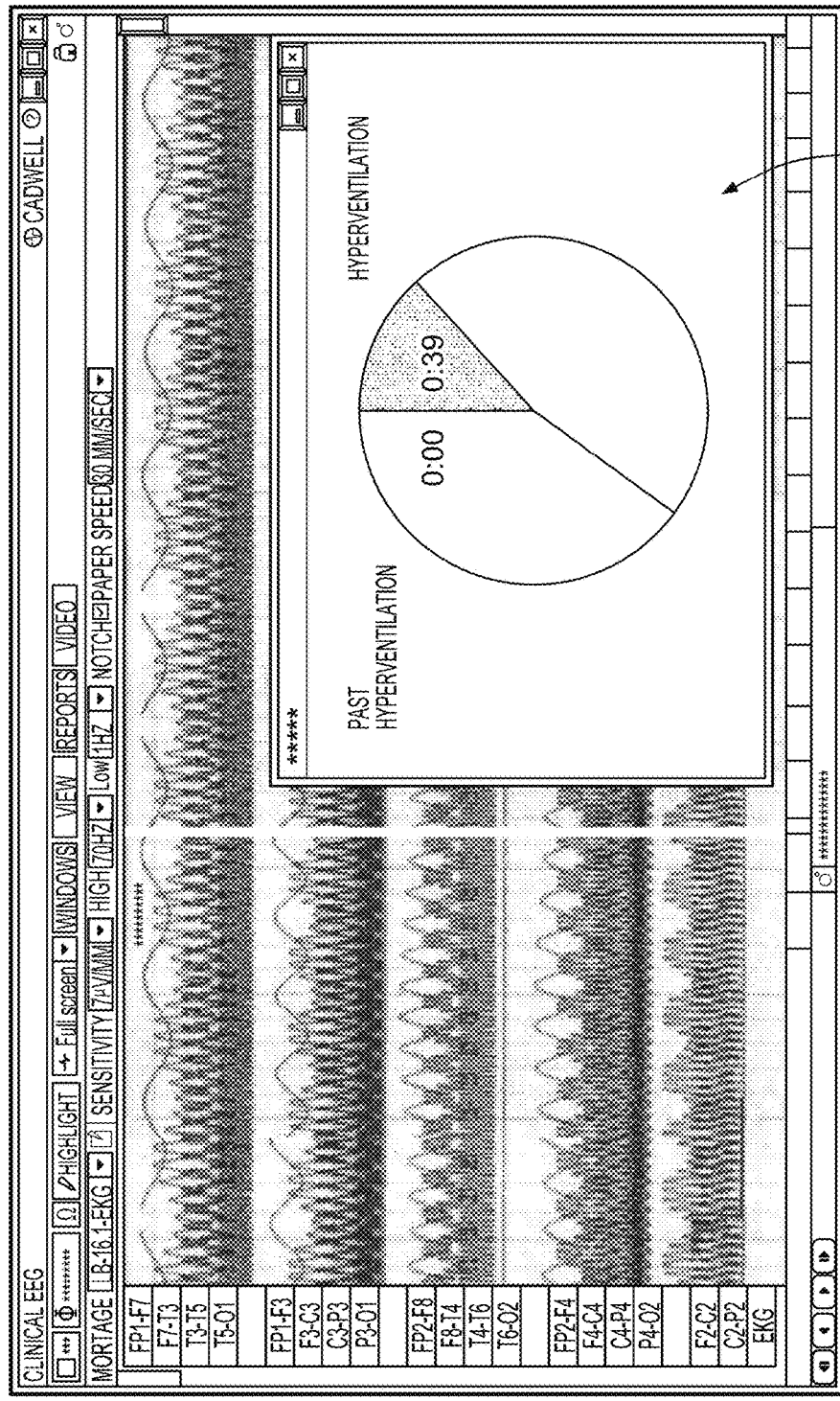
FIG. 14 shows another illustrative on-screen graphic indicating a progression of a subject through a hyperventilation period in accordance with some embodiments of the disclosure.

In FIG. 14, the guidance application generates (e.g., via control circuitry 404 (FIG. 4)) on-screen graphic 1402 in a resized and repositioned PIP window (e.g., as compared to on-screen graphic 1302 (FIG. 13)). For example, in response to a user input (e.g., received via user input interface 410 (FIG. 4)), the guidance application may change the size and/or position of on-screen graphic 1302 (e.g., in order for a practitioner to monitor both EEG data in region 1300 as well as on-screen graphic 1402).

Figure 15:
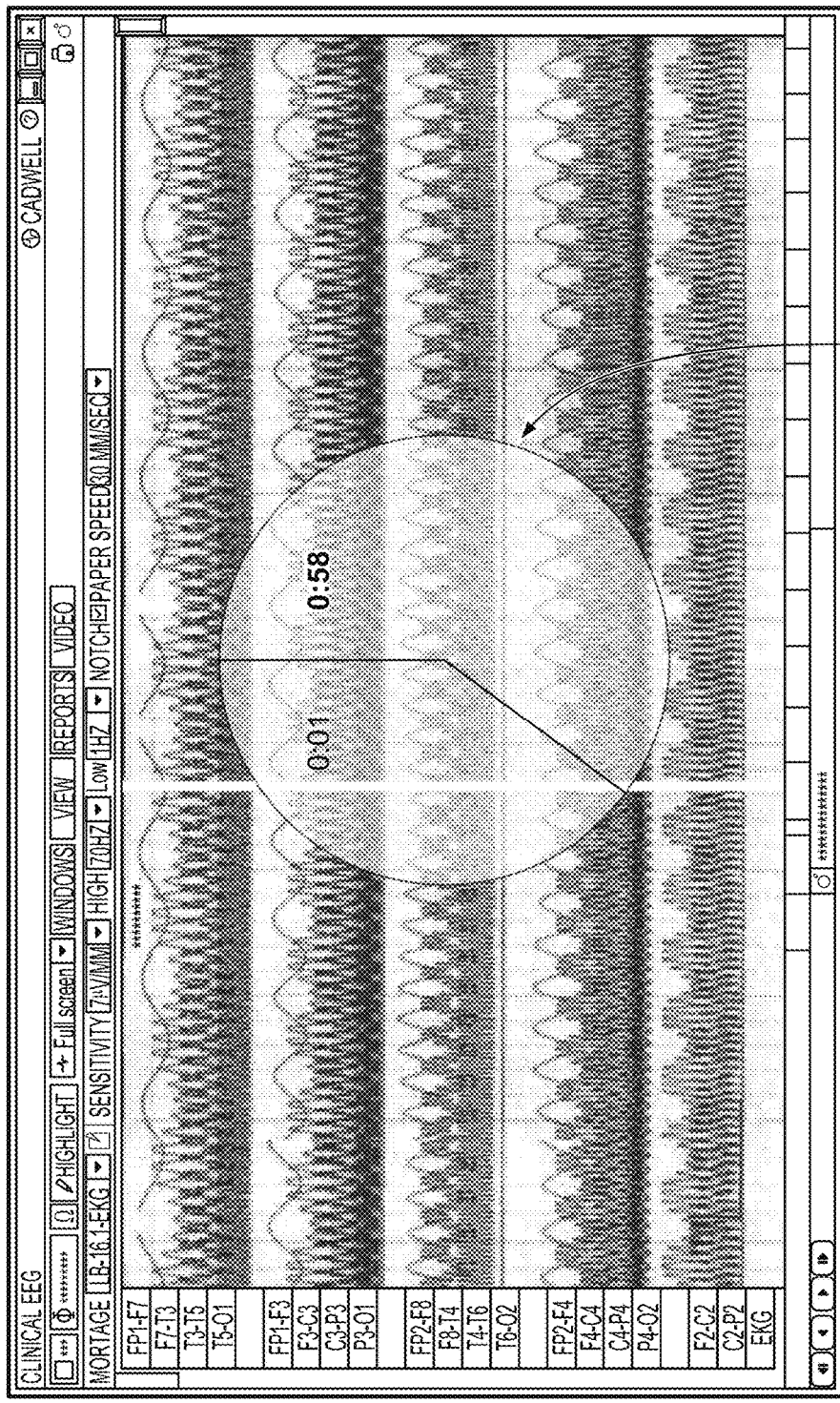
FIG. 15 shows an illustrative on-screen graphic indicating a progression of a subject from a hyperventilation period to a post-hyperventilation period in accordance with some embodiments of the disclosure.

FIG. 15 shows an illustrative on-screen graphic (e.g., generated for display on display 412 (FIG. 4)) indicating a progression of a subject from a hyperventilation period to a post-hyperventilation period. In FIG. 15, the guidance application (e.g., via control circuitry 404 (FIG. 4)) has generated for display on-screen graphic 1502 as a transparent overlay on top of region 1500. Additionally, the guidance application (e.g., via control circuitry 404 (FIG. 4)) has indicted that a subject has passed from a hyperventilation period to a post-hyperventilation period through the use of non-textual elements in on-screen graphic 1502. For example, in addition to indicating the amount of time that has progressed (e.g., via on-screen numbers), the guidance application has also used non-textual elements included in on-screen graphic 1502. For example, to indicate the transition of the subject from the hyperventilation period to the post-hyperventilation period, the guidance application may vary the color, shape, size, font, and/or other visual characteristic of a non-textual element. In FIG. 15, the guidance application generates for display on-screen graphic 1502 as a circle that is filled with pie chart slices that correspond to the amount of time a subject progresses through either a hyperventilation period or a post-hyperventilation period. While progressing in the hyperventilation period, the guidance application generates for display the slices in a first color. While progressing in the post-hyperventilation period, the guidance application generates for display the slices in a second color.

In some embodiments, the guidance application may trigger the transition from a hyperventilation period to a post-hyperventilation period automatically. For example, in response to determining that a selected amount of time for the hyperventilation period has expired, the guidance application may automatically transition to the post-hyperventilation period. Alternatively, guidance application may trigger the transition from a hyperventilation period to a post-hyperventilation period in response to a user input (e.g., received via user input interface 410 (FIG. 4)). For example, in response to determining that a subject needs to exit the hyperventilation period, a practitioner may manually trigger a post-hyperventilation period.

Figure 16:
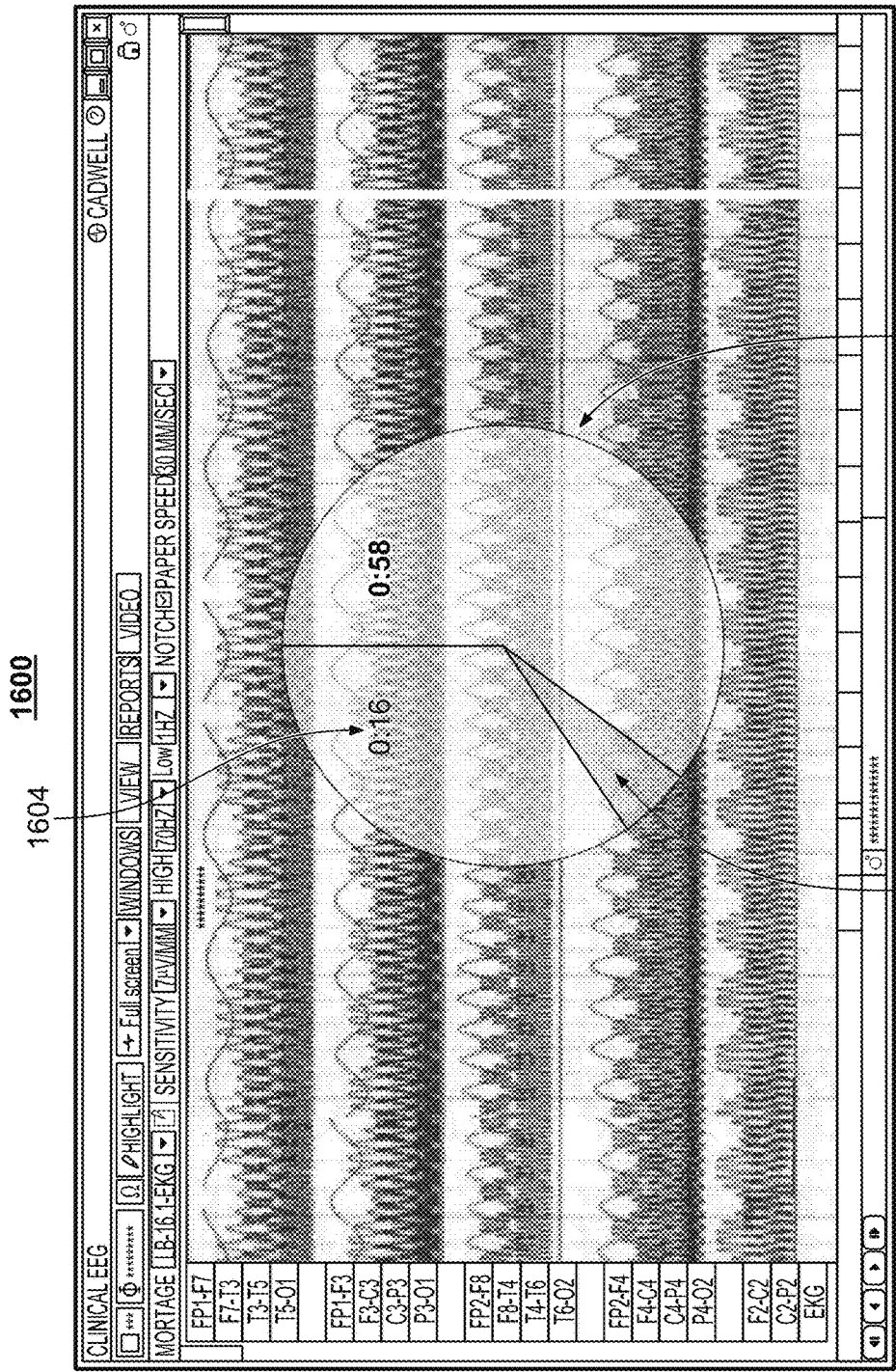
FIG. 16 shows an illustrative on-screen graphic indicating a progression of a subject through a post-hyperventilation period in accordance with some embodiments of the disclosure.

FIG. 16 shows an illustrative on-screen graphic (e.g., generated for display on display 412 (FIG. 4)) indicating a progression of a subject through a post-hyperventilation period. In FIG. 16, the guidance application has generated for display on-screen graphic 1602 as a transparent overlay on top of region 1600. Furthermore, the guidance application indicates the progress of a subject through the post-hyperventilation period through both textual element 1604 and non-textual element 1606. For example, the guidance application may indicate the progress of a user through an on-screen timer (e.g., textual element 1604) and/or through an animation of on-screen graphic 1602 (e.g., non-textual element 1606).

Figure 17:
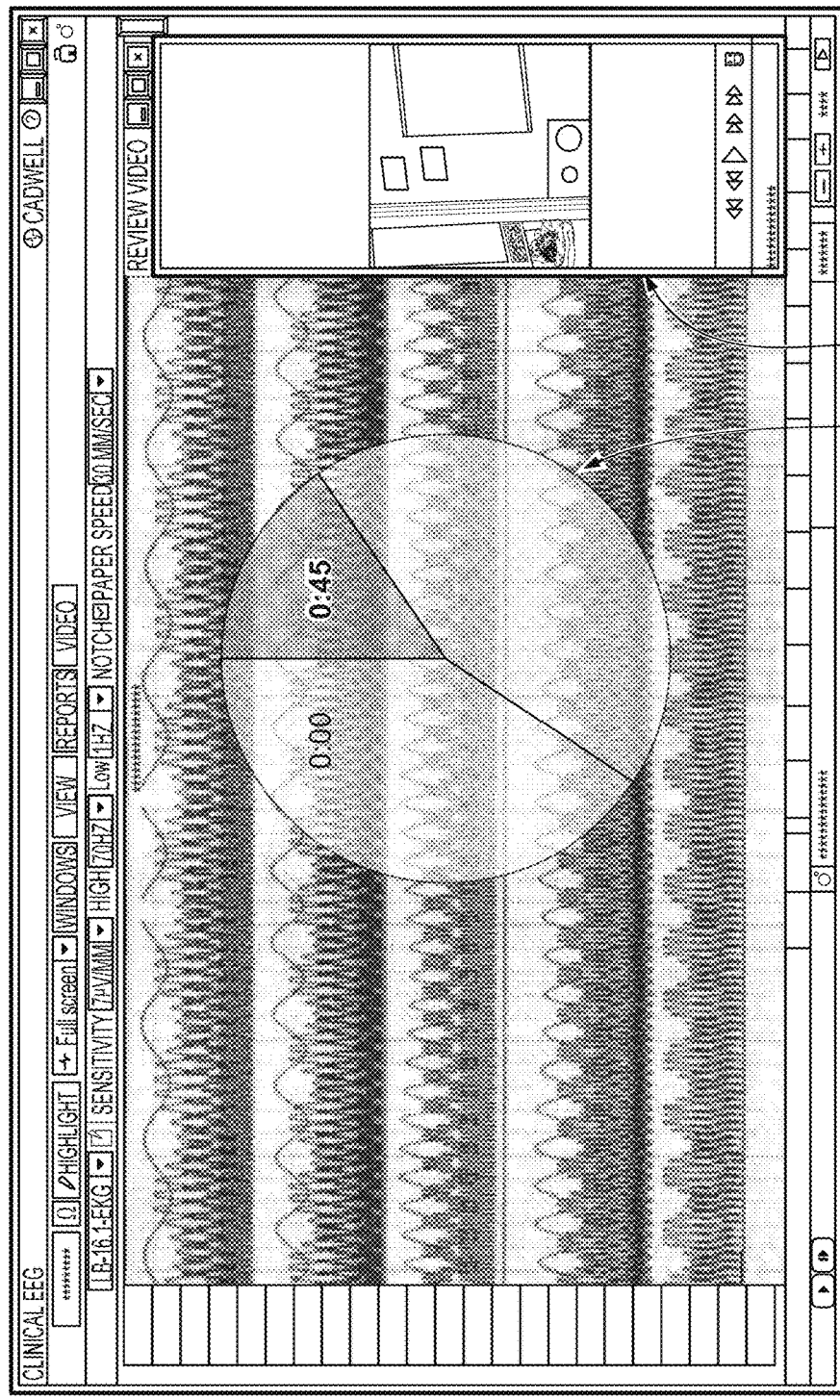
FIG. 17 shows an illustrative display screen with a first region featuring EEG data, a second region featuring video data, and an on-screen graphic indicating a progression of the subject through the hyperventilation period and the post-hyperventilation period in accordance with some embodiments of the disclosure.

FIG. 17 shows an illustrative display screen (e.g., display 412 (FIG. 4)) with first region 1700 featuring EEG data in a graphical representation, second region 1704 featuring video data, and on-screen graphic 1702 indicating a progression of the subject through the hyperventilation period and the post-hyperventilation period. For example, after receiving EEG data while a subject progressed through a hyperventilation period and a post-hyperventilation period, the guidance application may receive a user input (e.g., via user input interface 410 (FIG. 4)) navigating to a particular EEG instance (e.g., as discussed above). In addition to generating for display a portion of video data corresponding to the EEG instance, the guidance application may also generate for display an on-screen graphic (e.g., on-screen graphic 1702) that indicates a point of progression through a hyperventilation period or a post-hyperventilation period corresponding to the EEG instance. For example, in response to a user selection of a particular voltage fluctuation, the guidance application may synchronize and display video data (e.g., indicative of a physical manifestation associated with the voltage fluctuation) and/or an on-screen graphic (e.g., indicating whether or not a user was hyperventilating at the time of the voltage fluctuation).

Figure 18:
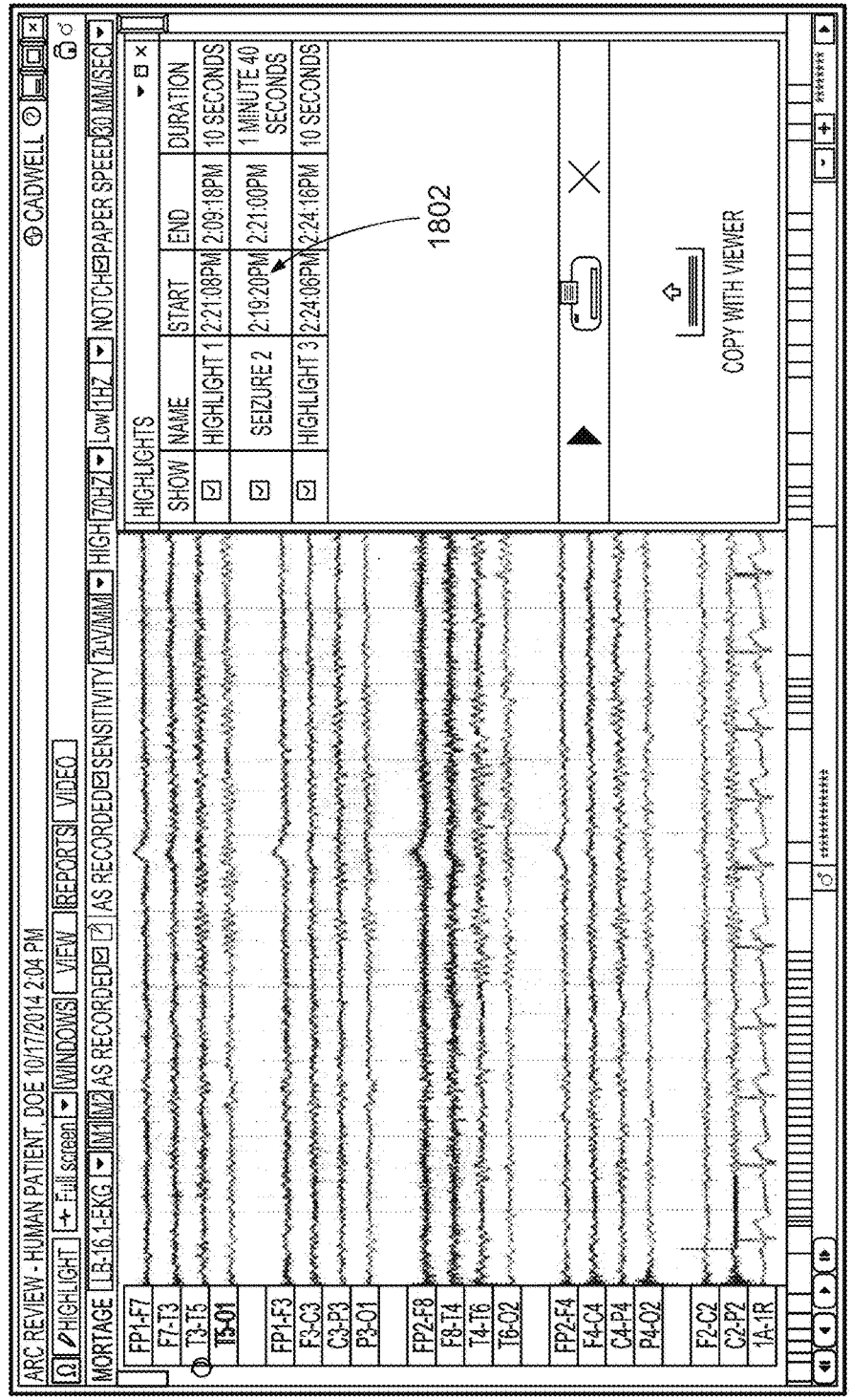
FIG. 18 shows an illustrative display screen featuring a plurality of selected portions of EEG data in accordance with some embodiments of the disclosure.

In some embodiments, the guidance application may highlight particular portions of EEG data. For example, a portion of EEG data may include voltage fluctuations, physical manifestations, etc. that are of interest to a practitioner. Accordingly, the guidance application may allow a user to highlight those portions. FIG. 18 shows an illustrative display screen featuring a plurality of selected portions. For example, in FIG. 18, region 1800 is situated adjacent to selectable portions 1802. Selectable portions 1802 may corresponds to portions of EEG data that were selected by a practitioner (e.g., via user input interface 410 (FIG. 4)). For example, the guidance application may receive a first user input identifying a beginning of a selectable portion and a second user input indicating an end of the selectable portion. The guidance application may then present links to those portions as selectable portions 1802.

Figure 19:
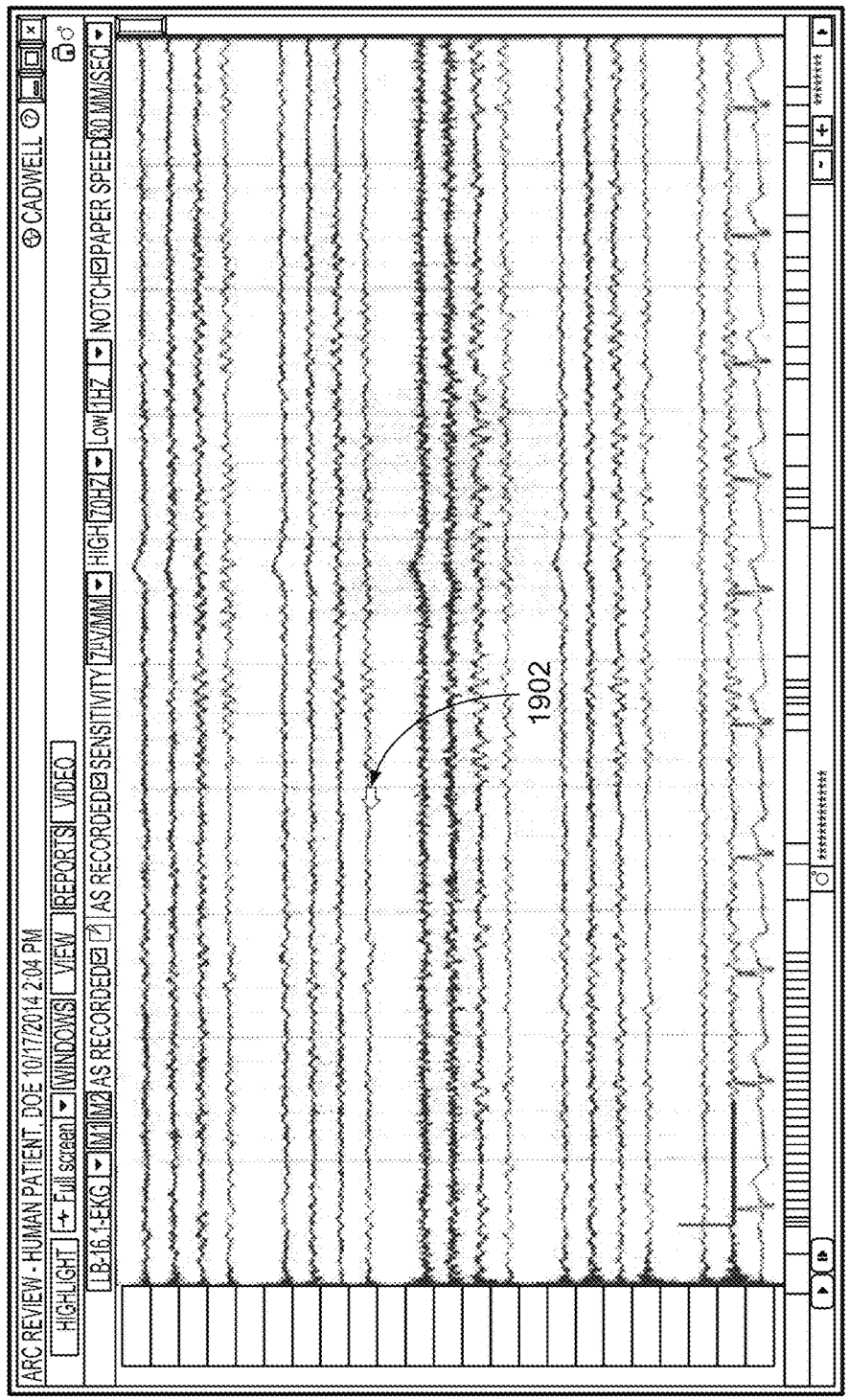
FIG. 19 shows an illustrative display screen featuring a selection of a portion of EEG data in accordance with some embodiments of the disclosure.
Figure 20:
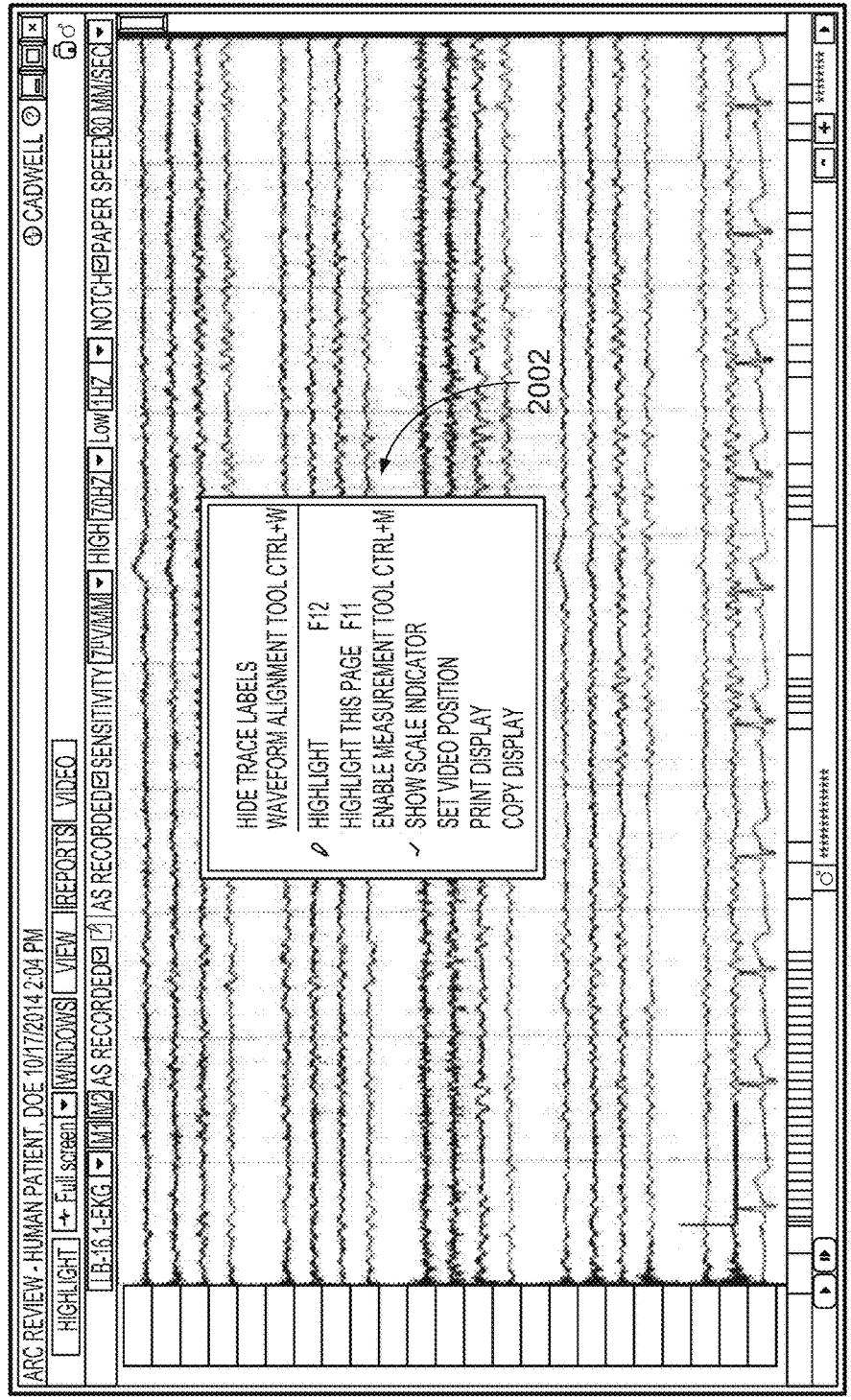
FIG. 20 shows an illustrative display screen featuring an on-screen option for selecting a portion of EEG data in accordance with some embodiments of the disclosure.

FIG. 19 shows an illustrative display screen (e.g., display 412 (FIG. 4)) in which on-screen cursor 1902 has selected a beginning point of a selectable portion from the EEG data in region 1900. In response, the guidance application may generate for display the options list 2002 overlaid on region 2000 as shown in FIG. 20. From options list 2002, the guidance application may receive a user input (e.g., via user input interface 410 (FIG. 4)) designating a beginning point of a selectable portion (e.g., corresponding to the location of on-screen cursor 1902 (FIG. 19)).

Figure 21:
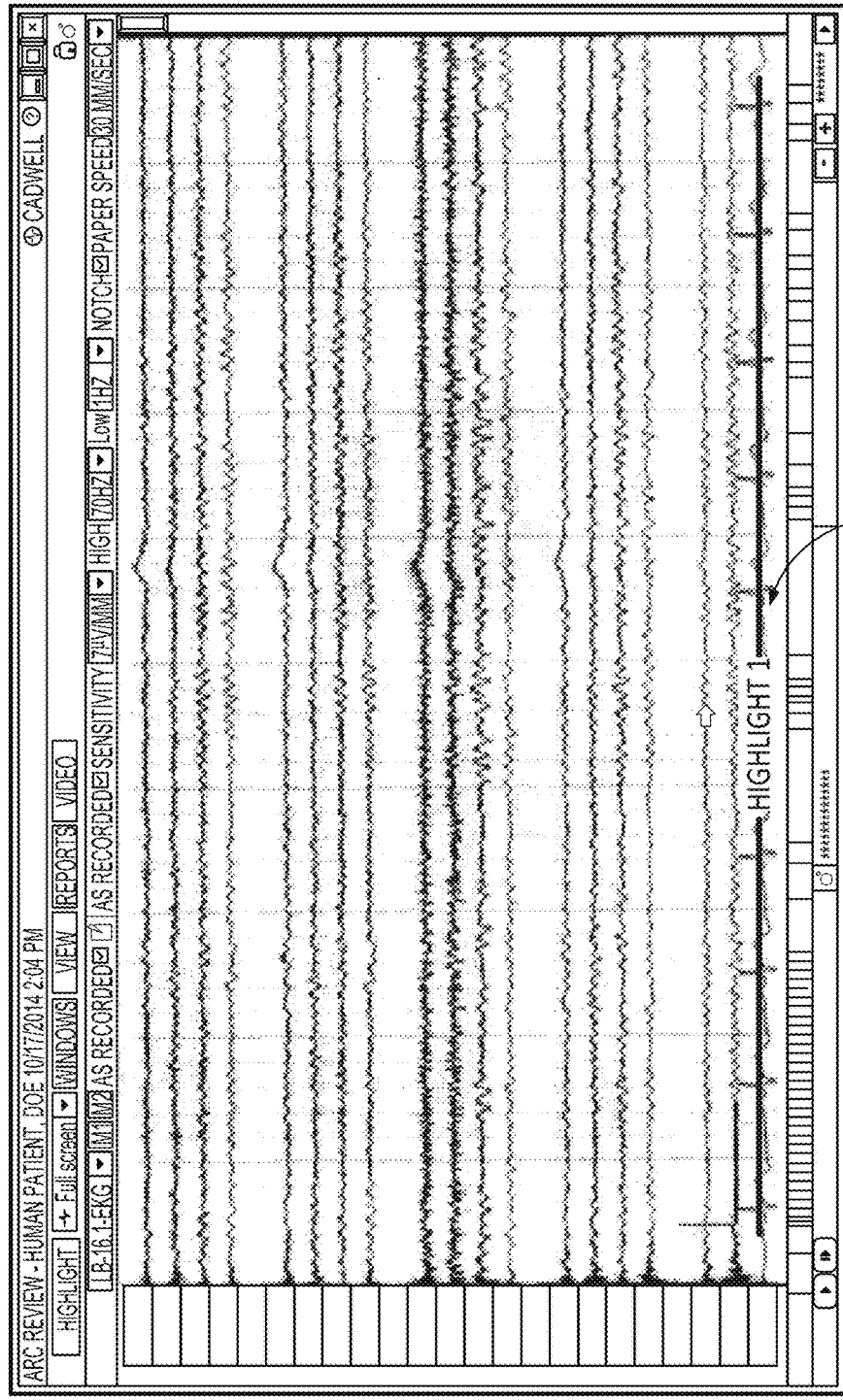
FIG. 21 shows an illustrative display screen featuring a selected portion of EEG data in accordance with some embodiments of the disclosure.
Figure 22:
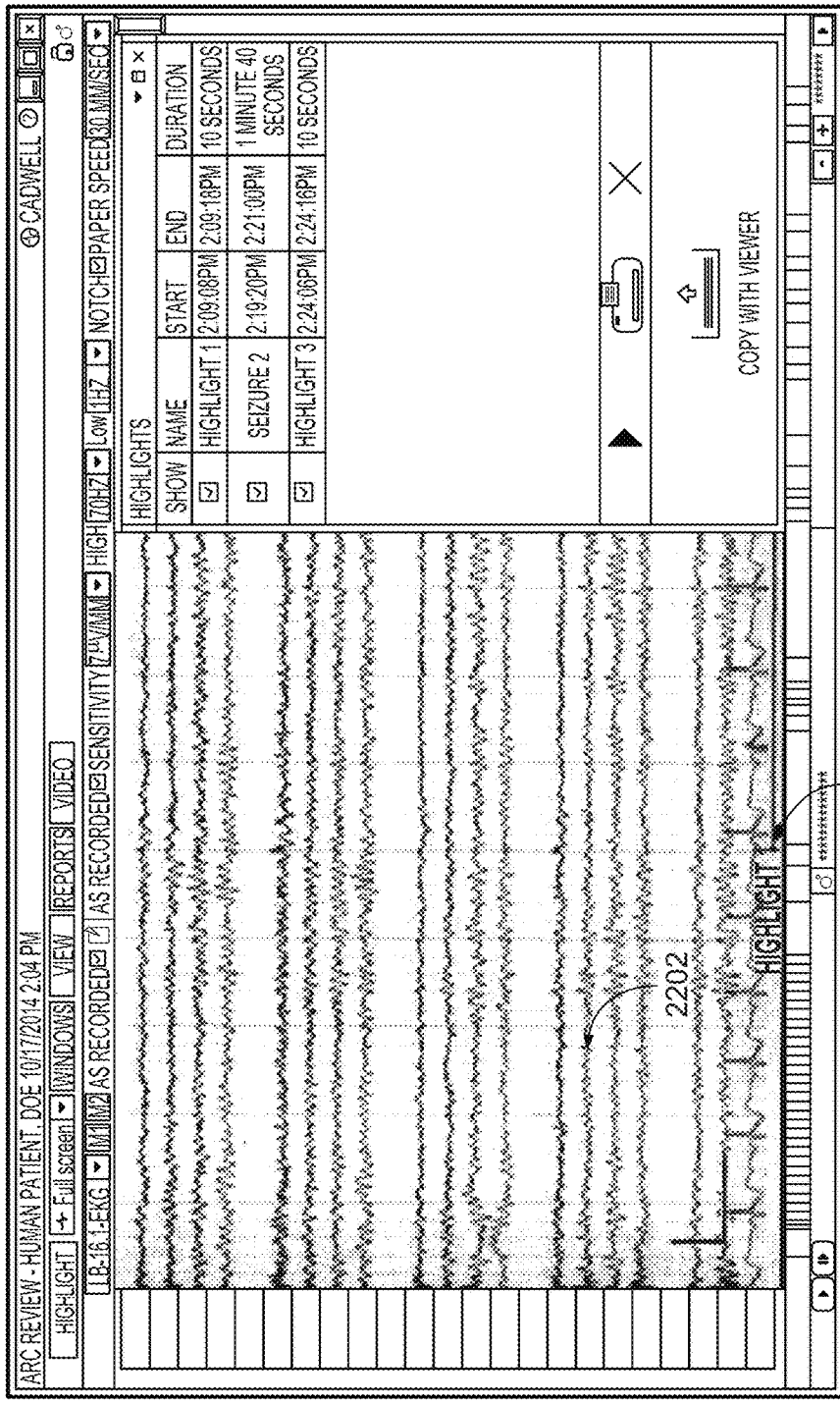
FIG. 22 shows an illustrative display screen featuring a selected portion of EEG data and an adjacent unselected portion in accordance with some embodiments of the disclosure.

FIG. 21 shows an illustrative display screen (e.g., display 412 (FIG. 4)) featuring a selected portion of EEG data. For example, as shown by indicator 2102, the EEG data currently shown in region 2100 is associated with a selectable portion. Indicator 2102 is currently shown as a solid line across the bottom of region 2100. However, it should be noted that indicator 2102 may, in some embodiments, include any audio and/or visual cue that alerts a user to the fact that EEG data is associated with a selectable portion. As shown in FIG. 22, the guidance application may indicate EEG data that does not corresponds to a selectable portion (e.g., EEG data 2202 in region 2200) by not generating for display an indicator (e.g., indicator 2204).

Figure 23:
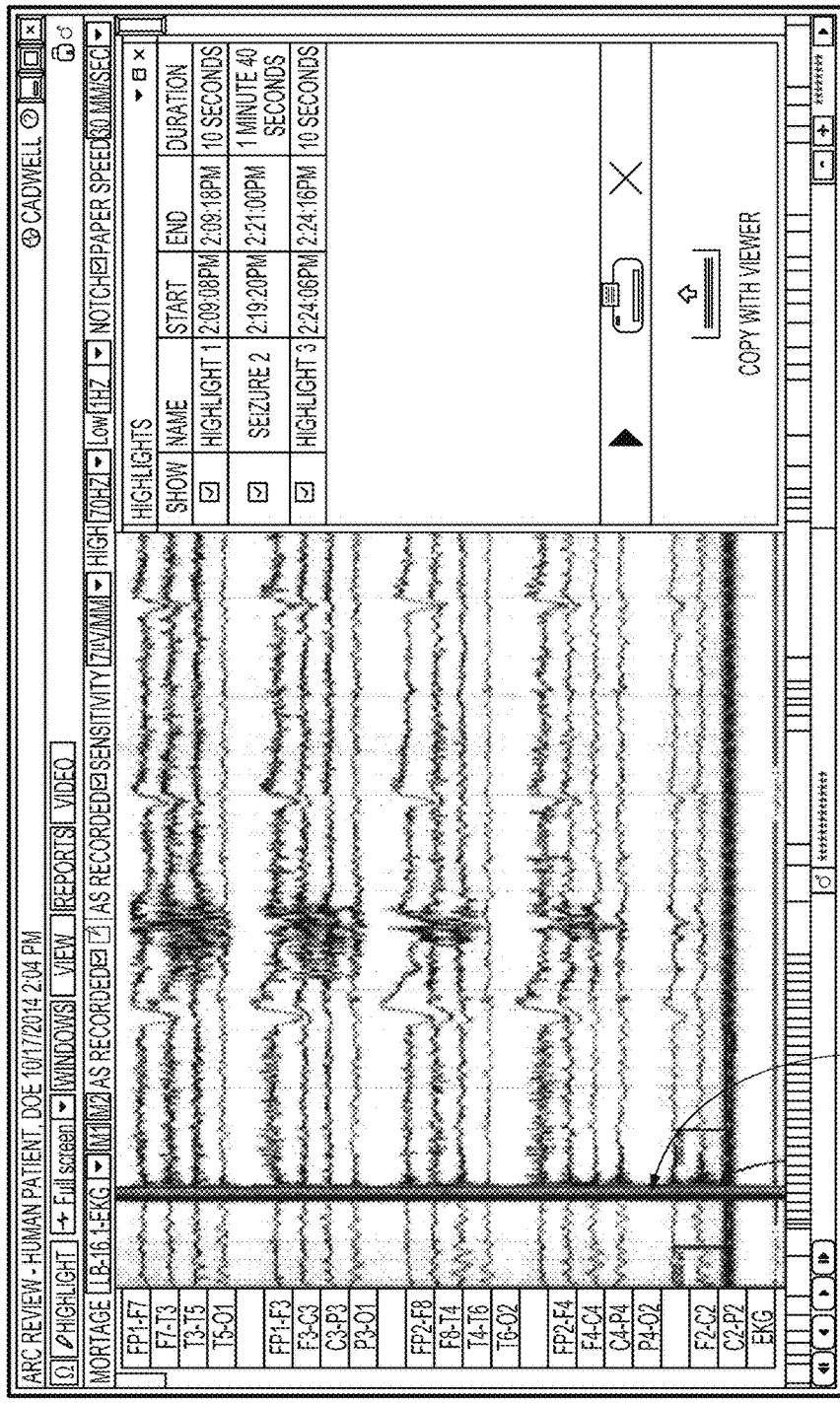
FIG. 23 shows an illustrative display screen featuring a truncated display of EEG data in accordance with some embodiments of the disclosure.

FIG. 23 shows an illustrative display screen (e.g., display 412 (FIG. 4)) featuring a truncated display of EEG data. For example, in some embodiments, in order to facilitate review of select EEG data, the guidance application may present the EEG data in a truncated version. The truncated version may show only selected portions of EEG data with the remaining portions being hidden from view. Accordingly, the guidance application provides an interface through which a practitioner can easily review only the most relevant portions of the EEG data.

Figure 24:
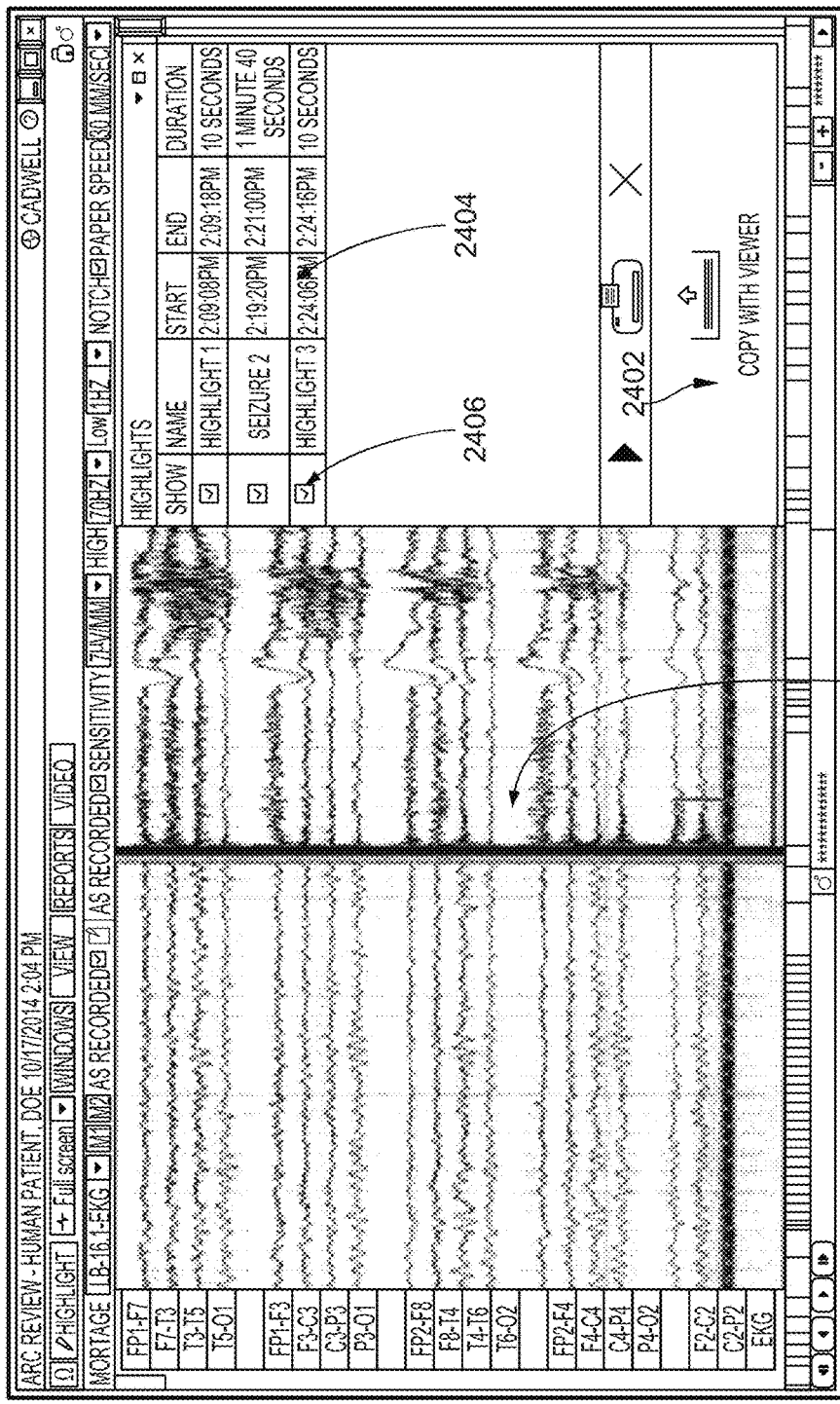
FIG. 24 shows an illustrative display screen featuring a user adjustment to a truncated display of EEG data in accordance with some embodiments of the disclosure.

The guidance application may generate for display truncation bar 2302 on region 2300, which indicates the order between two selected portions. The guidance application further allows unselected EEG data to be intuitively explored while its relation to the selected EEG is preserved. For example, as shown in FIG. 24, the guidance application may receive a user input (e.g., via user input interface 410 (FIG. 4)) that triggers adjustment to a truncated display of EEG data. For example, the guidance application may allow a user to interactively slide truncation bar 2402 about region 2400 to reveal EEG that was not included in a selectable portion.

FIG. 25 shows a flowchart of illustrative steps for determining video data that corresponds to a selected EEG instance. It should be noted that process 2500 or any step thereof could be performed on, or provided by, any of the devices shown in FIGS. 1-4. For example, process 2500 may be executed by control circuitry 404 (FIG. 4) as instructed by a guidance application implemented on user equipment 400 (FIG. 4) in order to determine video data that corresponds to a selected EEG instance. In addition, one or more steps of process 2500 may be incorporated into or combined with one or more steps of any other process or embodiment (e.g., process 2600 (FIG. 26)).

At step 2502, the guidance application receives (e.g., via I/O path 402 (FIG. 4)) EEG data comprising a plurality of EEG channels, in which each EEG channel of the plurality of EEG channels comprises a plurality of EEG instances. For example, to monitor brain activity of a subject, the guidance application may receive EEG data from multiple electrodes attached to the scalp of the subject, in which each electrode corresponds to a particular channel. Furthermore, each channel may correspond to real-time voltage fluctuations in the brain activity of the user.

At step 2504, the guidance application receives (e.g., via I/O path 402 (FIG. 4)) video data of a subject from which the received EEG data is based. For example, in addition to monitoring brain activity of the user (e.g., via control circuitry 404 (FIG. 4)), the guidance application may monitor physical manifestations by generating a video recording of the user.

At step 2506, the guidance application correlates (e.g., via control circuitry 404 (FIG. 4)) each EEG instance of the plurality of EEG instances to a respective portion of the video data in a database (e.g., storage 408 (FIG. 4)). For example, the guidance application may generate (e.g., via control circuitry 404 (FIG. 4)) a time stamp for each EEG instance, each of which corresponds to a time stamp for a portion of the video data.

At step 2508, the guidance application receives a first user input selecting a first EEG instance of the plurality of EEG instances. For example, the guidance application may receive a user input (e.g., via user input interface 410 (FIG. 4)) selecting a particular EEG instance (e.g., corresponding to a large voltage fluctuation) for which a practitioner wishes to examine a physical manifestation of the subject.

At step 2510, in response to receiving the first user input, the guidance application cross-references (e.g., via control circuitry 404 (FIG. 4)) the first EEG instance with the database to determine a first portion of the video data that corresponds to the first EEG instance. For example, the guidance application may determine (e.g., via control circuitry 404 (FIG. 4)) the time stamp corresponding to the EEG instance and match it with a time stamp corresponding to a portion of the video data.

At step 2512, the guidance application generates for display, on a display device, the first portion. For example, in response to the request of the practitioner to view the physical manifestation of a large voltage fluctuation in the EEG data, the guidance application presents (e.g., via control circuitry 404 (FIG. 4)) a portion of video data that corresponds to the large voltage fluctuation.

In some embodiments, the guidance application may continue to generate for display (e.g., via control circuitry 404 (FIG. 4)) the first portion until the end of the video data or until the guidance application receives a second user input (e.g., corresponding to a second EEG instance), at which point the first portion is replaced with a second portion of the video data (e.g., corresponding to second EEG instance).

In some embodiments, the guidance application may generate for display (e.g., via control circuitry 404 (FIG. 4)) a graphical representation of each EEG channel in a region of the display screen. The guidance application further divide the region (e.g., via control circuitry 404 (FIG. 4)) into a plurality of sub-regions, in which each sub-region corresponds to a particular portion of the video data and/or EEG instances with a particular time stamp.

It is contemplated that the steps or descriptions of FIG. 25 may be used with any other embodiment of this disclosure. In addition, the steps and descriptions described in relation to FIG. 25 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 1-4 could be used to perform one or more of the steps in FIG. 25.

Figure 26:
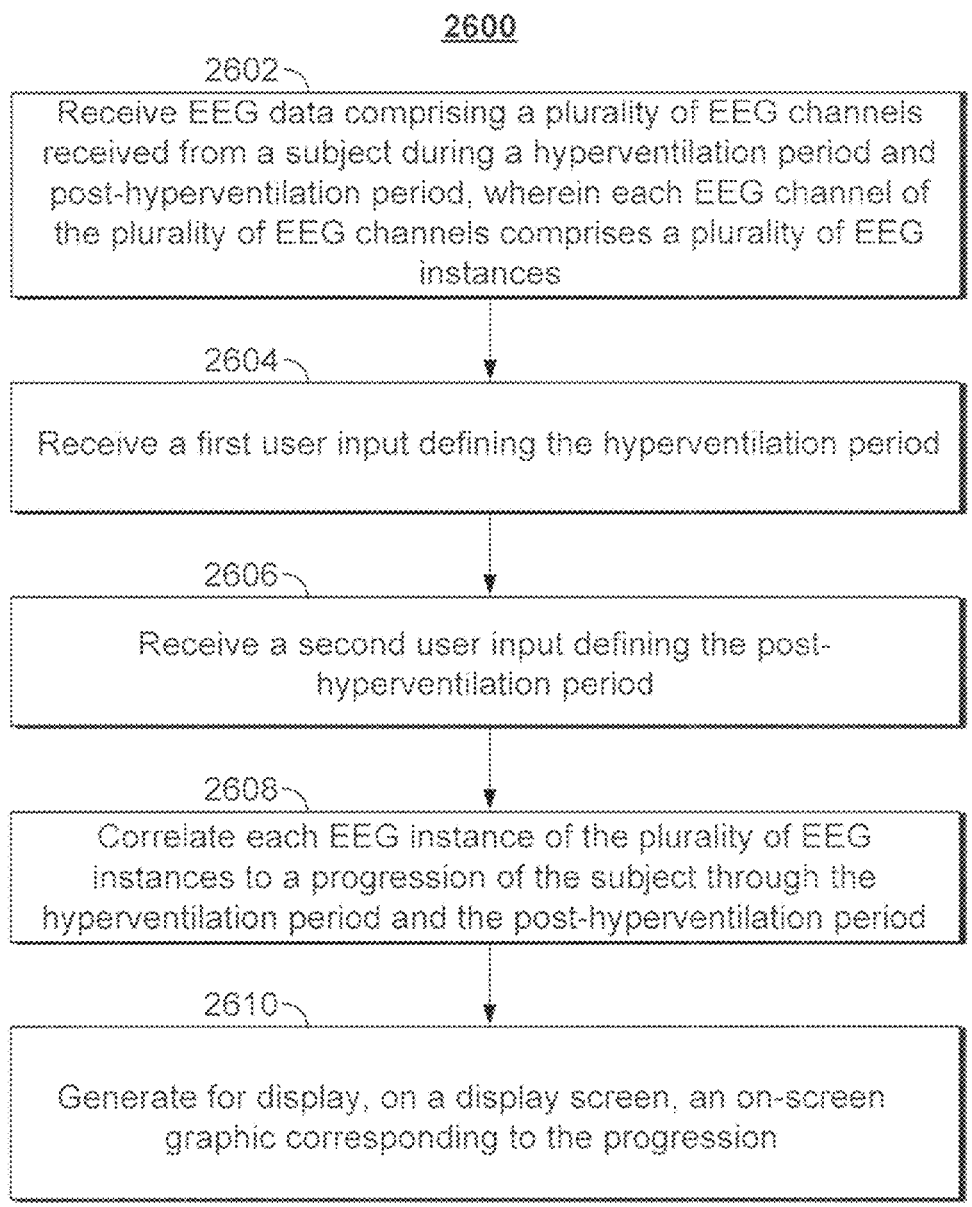
FIG. 26 shows a flowchart of illustrative steps for generating for display an on-screen graphic in accordance with some embodiments of the disclosure.

FIG. 26 shows a flowchart of illustrative steps for generating for display an on-screen graphic. It should be noted that process 2600 or any step thereof could be performed on, or provided by, any of the devices shown in FIGS. 1-4. For example, process 2600 may be executed by control circuitry 404 (FIG. 4) as instructed by a guidance application implemented on user equipment 400 (FIG. 4) in order to generate for display an on-screen graphic. In addition, one or more steps of process 2600 may be incorporated into or combined with one or more steps of any other process or embodiment (e.g., process 2500 (FIG. 25)).

At step 2602, the guidance application receives (e.g., via I/O path 402 (FIG. 4)) electroencephalography data comprising a plurality of EEG channels received from a subject during a hyperventilation period and post-hyperventilation period, in which each EEG channel of the plurality of EEG channels comprises a plurality of EEG instances. For example, to monitor brain activity of a subject, the guidance application may receive EEG data from multiple electrodes attached to the scalp of the subject, in which each electrode corresponds to a particular channel. Furthermore, each channel may correspond to real-time voltage fluctuations in the brain activity of the user.

At step 2604, the guidance application receives a first user input (e.g., via user input interface 410 (FIG. 4)) defining the hyperventilation period and, at step 2606, the guidance application receives (e.g., via user input interface 410 (FIG. 4)) a second user input defining the post-hyperventilation period. For example, the guidance application may receive an input from the practitioner indicating how long a subject should remain in a hyperventilation state as well as how long the subject needs to recover.

At step 2608, the guidance application correlates (e.g., via control circuitry 404 (FIG. 4)) each EEG instance of the plurality of EEG instances received in incoming EEG data to a progression of the subject through the hyperventilation period and the post-hyperventilation period. For example, the guidance application may both receive and record incoming EEG data, but also manage the progression of the subject through the hyperventilation period and the post-hyperventilation period.

At step 2610, the guidance application generates for display, on a display screen, an on-screen graphic corresponding to the progression. For example, in order to allow the practitioner to analyze the incoming EEG without losing track of the length of the hyperventilation of the user, the guidance application may generate an on-screen graphic that intuitively informs the practitioner of the progress of the subject. For example, the on-screen graphic may include a first portion that corresponds to the hyperventilation period and a second portion that corresponds to the post-hyperventilation period.

In some embodiments, to increase the intuitiveness of the on-screen graphic and to reduce the reliance on textual elements (which may require a greater amount of the attention of the practitioner to monitor), the on-screen graphic may include one or more non-textual elements that indicates the progression of the subject through the hyperventilation period and the post-hyperventilation period. For example, the guidance application may determine whether the progression corresponds to a hyperventilation period or a post-hyperventilation period and modify the characteristics (e.g., size, shape, color, etc.) of the textual elements accordingly.

It is contemplated that the steps or descriptions of FIG. 26 may be used with any other embodiment of this disclosure. In addition, the steps and descriptions described in relation to FIG. 26 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 1-4 could be used to perform one or more of the steps in FIG. 26.

Figure 27:
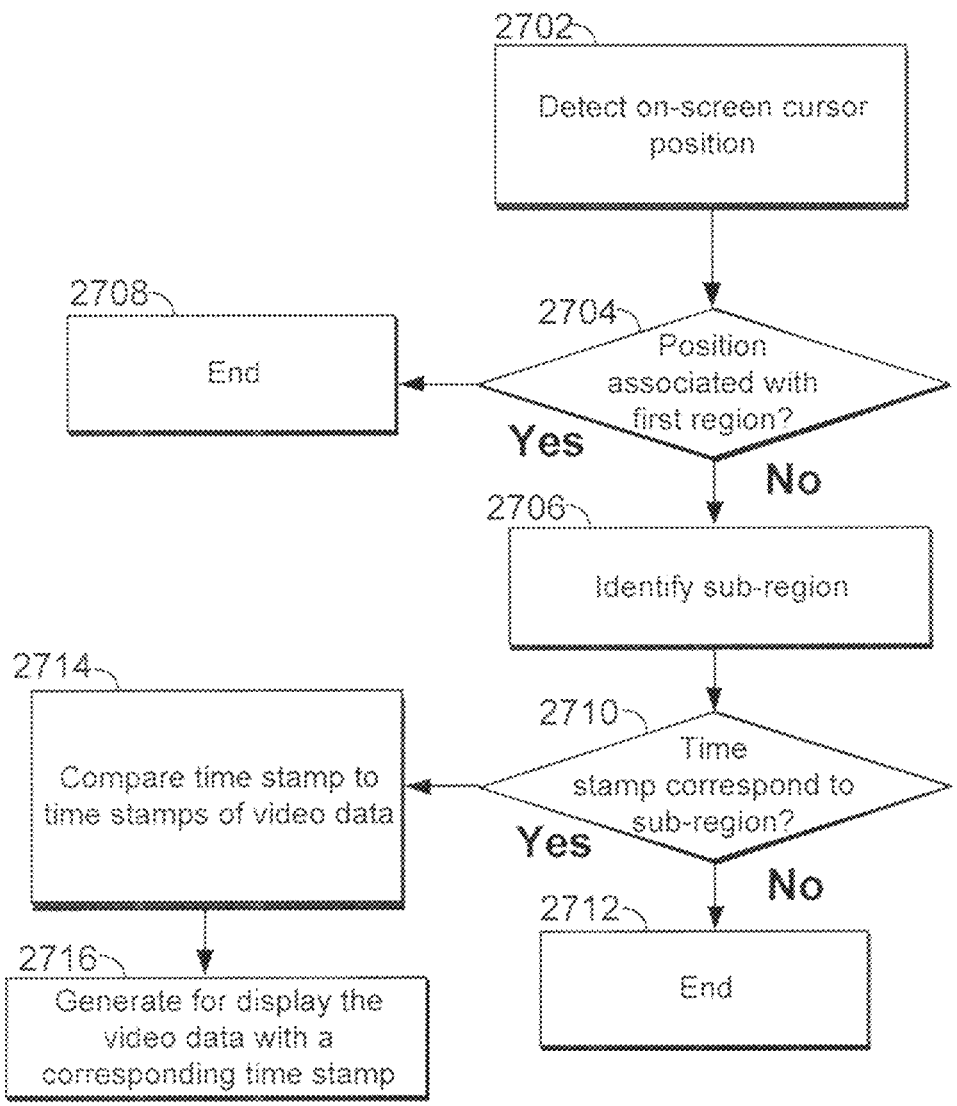
FIG. 27 shows a flowchart of illustrative steps for correlating EEG data and video data in accordance with some embodiments of the disclosure.

FIG. 27 shows a flowchart of illustrative steps for correlating EEG data and video data. It should be noted that process 2700 or any step thereof could be performed on, or provided by, any of the devices shown in FIGS. 1-4. For example, process 2700 may be executed by control circuitry 404 (FIG. 4) as instructed by a guidance application implemented on user equipment 400 (FIG. 4) in order to correlate EEG data and video data. In addition, one or more steps of process 2700 may be incorporated into or combined with one or more steps of any other process or embodiment (e.g., process 2500 (FIG. 25)).

At step 2702, the guidance application detects (e.g., via control circuitry 404 (FIG. 4)) an on-screen cursor position. For example, the guidance application may receive a user input (e.g., via user input interface 410 (FIG. 4)) navigating an on-screen cursor (e.g., on-screen cursor 702 (FIG. 7)) about a display screen (e.g., display 412 (FIG. 4)). The guidance application may determine (e.g., via control circuitry 404 (FIG. 4)) a coordinate (e.g., an x, y coordinate) of the on-screen cursor as a result of the user input.

At step 2704, the guidance application determines (e.g., via control circuitry 404 (FIG. 4)) whether or not the position is associated with a first region (e.g., first region 500 (FIG. 5)). For example, a user input (e.g., receive via user input interface 410 (FIG. 4)) may result in the guidance application positioning an on-screen cursor in a region that has a graphical representation of EEG data. If so, the guidance application may automatically correlate the EEG data corresponding to the position of the on-screen cursor with video data. In contrast, if the position is not associated with a region featuring a graphical representation of EEG data (e.g., the on-screen cursor is hovering over video region 506 (FIG. 5)), the guidance application may not automatically correlate the EEG data corresponding to the position of the on-screen cursor with video data. If the position is not associated with a first region, the guidance application ends process 2700 at step 2708. If the position is associated with a first region, the guidance application proceeds to step 2706.

At step 2706, the guidance application identifies (e.g., via control circuitry 404 (FIG. 4)) a sub-region corresponding to the position of the on-screen cursor. For example, the guidance application may subdivide the first region (e.g., a graphical representation of EEG data) into a plurality of sub-regions. Each sub-region may correspond to a distinct set of EEG data (e.g., EEG data corresponding to a particular time stamp).

At step 2708, the guidance application determines (e.g., via control circuitry 404 (FIG. 4)) whether or not a time stamp corresponds to the sub-region. For example, the guidance application may cross-reference the sub-region with a database (e.g., located at storage 408 (FIG. 4)) listing time stamps for sub-regions to determine a time stamp (e.g., a value reflecting a time when the EEG in the sub-region was received) for the sub-region. If the guidance application fails to identify a time stamp for the sub-region, process 2700 proceeds to step 2712 and ends.

If the guidance application identifies a time stamp for the sub-region, the guidance application proceeds to step 2714 and compares the time stamp for the sub-region to times stamps corresponding to video data. For example, the guidance application may cross-reference the time stamp for the sub-region with a database (e.g., located at storage 408 (FIG. 4)) listing time stamps for portions of video data to determine a time stamp (e.g., a value reflecting a time when the portion of video data was recorded/received) for the sub-region. For example, the database may be structured as a look-up table database. The guidance application may filter the available time stamps for video data based on whether or not the available time stamps match the time stamp of the sub-region. The database may then output a portion of video data that corresponds to the time stamp of the sub-region.

At step 2716, the guidance application generates for display (e.g., on display 412 (FIG. 4) the video data with a corresponding time stamp. For example, in response to detecting an on-screen cursor is hovering above a portion of EEG data in a first region (e.g., first region 500 (FIG. 5)), the guidance application may generate for display corresponding video data in a second region (e.g., video region 506 (FIG. 5)).

It is contemplated that the steps or descriptions of FIG. 27 may be used with any other embodiment of this disclosure. In addition, the steps and descriptions described in relation to FIG. 27 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 1-4 could be used to perform one or more of the steps in FIG. 27.

As described with respect to FIG. 18, the guidance application allows for particular portions of the EEG data to be highlighted. The guidance application may present links to these highlighted portions as selectable portions. The links to the highlighted portions may be uniquely identified by patient information associated with EEG records and video corresponding to the highlighted portions. In some embodiments, these highlighted portions can be copied and exported to be viewed without the guidance application. When the records corresponding to the highlighted portions are exported, it may be advantageous to anonymize the patient information to protect the patient.

Figure 28:
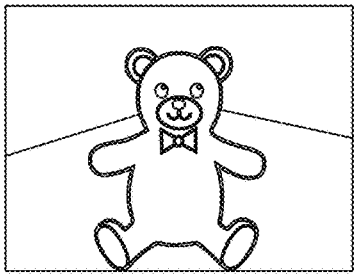
FIG. 28 shows an illustrative display screen indicating a patient information form in accordance with some embodiments of the disclosure.

FIG. 28 shows an illustrative display screen (e.g., generated for display on display 412 (FIG. 4)) indicating a Patient Information Form 2800. This form is used to store information of the patient undergoing the EEG. This information is stored along with the EEG waves and the video of the patient and is used to uniquely identify each EEG record stored in the guidance application. The stored patient information includes, but is not limited to, Last Name 2802, First Name 2804, Patient ID 2808, Birthdate 2810, Age 2818, Gender 2812, and Handedness 2814. The patient information form may include different fields to be populated by the practitioner by selecting 'Custom' button 2820. This option may allow the practitioner to include any fields not included in the Patient Information Form 2800. Once the practitioner is satisfied with the information entered, he or she can select the 'Save' button 2816 to save the details corresponding to the patient in the guidance application for future reference.

Figure 29:
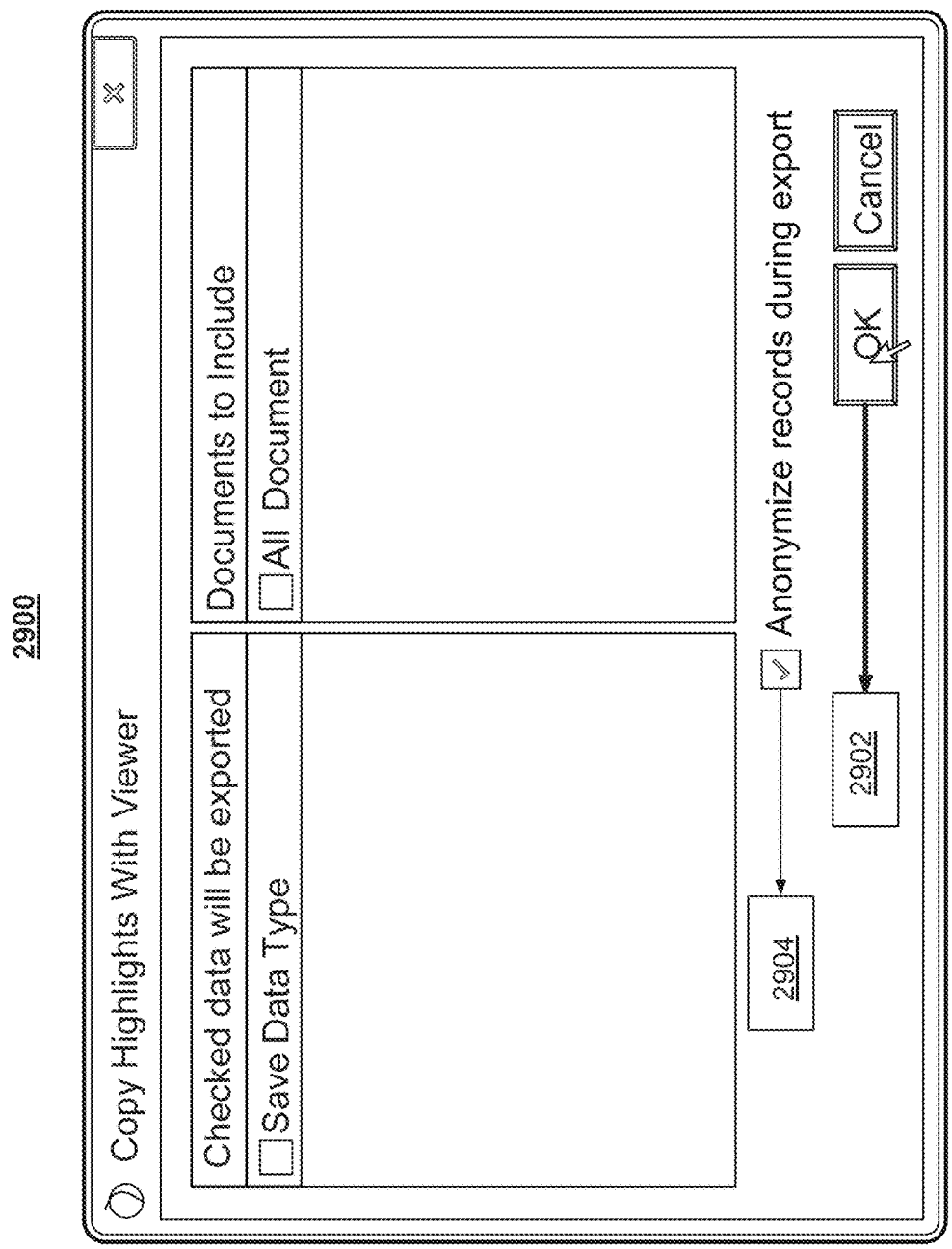
FIG. 29 shows an illustrative display screen indicating a window to copy a highlighted portion of EEG data in accordance with some embodiments of the disclosure.

FIG. 29 shows an illustrative display screen (e.g., generated for display on display 412 (FIG. 4)) indicating a window to copy a highlighted portion of EEG data. The process of highlighting a portion of EEG data is discussed in more detail with respect to FIG. 18. A copy of the highlighted portion of EEG data can be exported. The process of exporting a copy of the highlighted portion involves wrapping the copy of the highlighted portion in viewer software that allows the record to be viewed without the guidance application. In the process of exporting EEG data, patient information corresponding to the data is attached to the EEG data being exported. However, it is possible to anonymize the patient information before it is attached to the EEG data and exported. For example, by selecting button 2904, the practitioner informs the guidance application of his or her intent to anonymize the data before it is exported. Once the practitioner has made the selection to anonymize the EEG data, he or she selects 'OK' 2902 to proceed.

Figure 30:
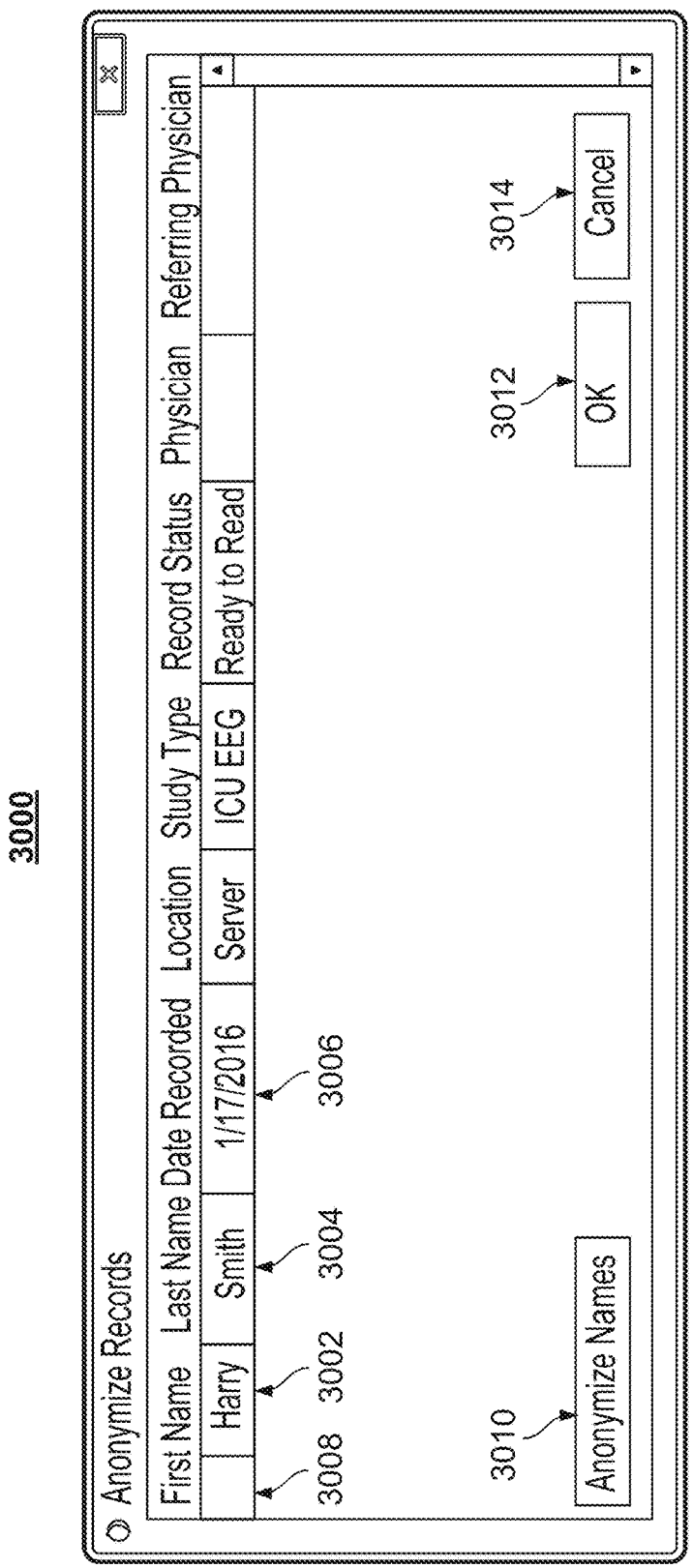
FIG. 30 shows an illustrative display screen indicating a window with patient records that is generated in response to user input in accordance with some embodiments of the disclosure.

FIG. 30 shows an illustrative display screen (e.g., generated for display on display 412 (FIG. 4)) indicating a window with patient records that is generated once the practitioner selects 'OK' 2902 in FIG. 29. Highlights associated with a given patient record are displayed in a list 2404 as seen in FIG. 24. Each highlight shown in this table is a highlight of EEG data corresponding to one patient record. The practitioner selects which highlights need to be copied with a viewer by checking the box 2406 next to the highlight and then selects 'COPY WITH VIEWER' 2402 in FIG. 24. As shown in the illustrative embodiment of FIG. 30, each record is identified with a First Name 3002, a Last Name 3004, Date recorded 3006. In some embodiments, it is possible that the records are identified with additional or different information. In order to select a record to be exported, the practitioner may select button 3008. Once the practitioner has selected the records to be exported, the practitioner may select Anonymize Names button 3010 to anonymize the patient information corresponding to the EEG data. In the event the practitioner wants to proceed without anonymizing EEG data, they can do so by deselecting the checkbox 2904 for Anonymize records during export and selecting OK 2902 in FIG. 29. As will be evident to one of skill in the art, the systems and methods described above are equally applicable to a single record for a single patient, multiple records for a single patient, and multiple records for each of multiple patients.

FIG. 31 shows an illustrative display screen (e.g., generated for display on display 412 (FIG. 4)) indicating a window containing anonymized records of EEG data ready to be exported. As shown in FIG. 31, the First Name field 3102 and Last Name field 3104 have a randomly generated string of characters instead of 'Harry' and 'Smith' as shown in FIG. 30. The anonymization process replaced the original first name and last name of the patient with randomly generated strings to preserve the patient's identity. Alternatively or additionally, the process of anonymization may allow the practitioner to manually specify values for the various fields he or she wishes to assign to the selected EEG records instead of having the guidance application randomly generate the necessary values. Once the practitioner is satisfied with the anonymized information, he or she can proceed to export the information by selecting the Export button 3108. It is noted that the process of anonymization of the EEG data does not affect the EEG records in the source database of the guidance application.

The above-described embodiments of the present disclosure are presented for purposes of illustration and not of limitation, and the present disclosure is limited only by the claims that follow. Furthermore, it should be noted that the features and limitations described in any one embodiment may be applied to any other embodiment herein, and flowcharts or examples relating to one embodiment may be combined with any other embodiment in a suitable manner, done in different orders, or done in parallel. In addition, the systems and methods described herein may be performed in real time. It should also be noted, the systems and/or methods described above may be applied to, or used in accordance with, other systems and/or methods.

What is claimed is:

1. A method of correlating brain activity to physical manifestations, the method comprising:
   receiving data indicative of at least one of a hyperventilation period or a post-hyperventilation period;
   receiving electroencephalography ("EEG") data comprising a plurality of EEG channels, wherein each EEG channel of the plurality of EEG channels comprises a plurality of EEG instances;
   receiving video data of a subject from which the received EEG data is based;
   correlating each EEG instance of the plurality of EEG instances to a respective portion of the video data in a database;
   receiving a first user input selecting a first EEG instance of the plurality of EEG instances;
   in response to receiving the first user input, cross-referencing the first EEG instance with the database to determine a first portion of the video data that corresponds to the first EEG instance;
   correlating the data indicative of the at least one of the hyperventilation period or the post-hyperventilation period with at least one of the plurality of EEG instances or the first portion of the video data; and
   generating for concurrent display, on a display device, the first portion of the video data, the plurality of EEG instances, and a graphic, separate from the plurality of EEG instances, that visually indicates a progression of the at least one of the hyperventilation period or the post-hyperventilation period correlated with the at least one of the plurality of EEG instances or the first portion of the video data.

2. The method of claim 1, further comprising:
   generating for display, on the display screen, a graphical representation of each EEG channel; and
   overlaying the first portion on the graphical representation of each EEG channel.

3. The method of claim 2, further comprising:
   generating for display the graphical representation of each EEG channel in a region of the display screen; and
   determining a plurality of sub-regions within the region, wherein a first sub-region of the plurality of sub-regions corresponds to the first portion.

4. The method of claim 3, further comprising:
   determining that the first EEG instance corresponds to the first sub-region;
   determining that a second EEG instance corresponds to the first sub-region; and
   generating for display the first portion in response to a user input selecting either the first EEG instance or the second EEG instance.

5. The method of claim 4, wherein the first EEG instance corresponds to a first EEG channel of the plurality of EEG channels and the second EEG instance corresponds to a second EEG channel of the plurality of EEG channels.

6. The method of claim 5, wherein the first user input selecting the first EEG instance of the plurality of EEG instances comprises hovering an on-screen icon in the first sub-region.

7. The method of claim 1, further comprising:
   while the first portion is generated for display, receiving a second user input selecting a second EEG instance of the plurality of EEG instances;
   in response to receiving the second user input, cross-referencing the second EEG instance with the database to determine a second portion of the video data that corresponds to the first EEG instance; and
   replacing, on the display device, the first portion with the second portion.

8. The method of claim 1, further comprising:
   generating a time stamp for the first instance that corresponds to a location in the received EEG data;
   generating a time stamp for the first portion that corresponds to a location of the first portion in the video data; and
   determining that the time stamp for the first instance corresponds to the time stamp for the first portion.

9. The method of claim 8, wherein the location in the received EEG data corresponds to a first sub-region of a plurality of sub-regions in a region of the display screen corresponding to a graphical representation of each EEG channel.

10. The method of claim 9, wherein the first sub-region corresponds to the first instance that corresponds to a first EEG channel of the plurality of EEG channels and a second EEG instance that corresponds to a second EEG channel of the plurality of EEG channels.

11. A system for correlating brain activity to physical manifestations, the system comprising:
   a database; and
   control circuitry configured to:
      receive data indicative of at least one of a hyperventilation period or a post-hyperventilation period;
      receive electroencephalography ("EEG") data comprising a plurality of EEG channels, wherein each EEG channel of the plurality of EEG channels comprises a plurality of EEG instances;

receive video data of a subject from which the received EEG data is based;

correlate each EEG instance of the plurality of EEG instances to a respective portion of the video data in a database;

receive a first user input selecting a first EEG instance of the plurality of EEG instances;

in response to receiving the first user input, cross-reference the first EEG instance with the database to determine a first portion of the video data that corresponds to the first EEG instance;

correlate the data indicative of the at least one of the hyperventilation period or the post-hyperventilation period with at least one of the plurality of EEG instances or the first portion of the video data; and generate for display, on a display device, the first portion of the video data, the plurality of EEG instances, and a graphic, separate from the plurality of EEG instances, that visually indicates a progression of the at least one of the hyperventilation period or the post-hyperventilation period correlated with the at least one of the plurality of EEG instances or the first portion of the video data.

12. The system for correlating brain activity to physical manifestations of claim 11, wherein the control circuitry is further configured to:

generate for display, on the display screen, a graphical representation of each EEG channel; and overlay the first portion on the graphical representation of each EEG channel.

13. The system for correlating brain activity to physical manifestations of claim 12, wherein the control circuitry is further configured to:

generate for display the graphical representation of each EEG channel in a region of the display screen; and determine a plurality of sub-regions within the region, wherein a first sub-region of the plurality of sub-regions corresponds to the first portion.

14. The system for correlating brain activity to physical manifestations of claim 13, wherein the control circuitry is further configured to:

determine that the first EEG instance corresponds to the first sub-region;

determine that a second EEG instance corresponds to the first sub-region; and generate for display the first portion in response to a user input selecting either the first EEG instance or the second EEG instance.

15. The system for correlating brain activity to physical manifestations of claim 14, wherein the first EEG instance corresponds to a first EEG channel of the plurality of EEG channels and the second EEG instance corresponds to a second EEG channel of the plurality of EEG channels.

16. The system for correlating brain activity to physical manifestations of claim 15, wherein the first user input selecting the first EEG instance of the plurality of EEG instances comprises hovering an on-screen icon in the first sub-region.

17. The system for correlating brain activity to physical manifestations of claim 11, wherein the control circuitry is further configured to:

while the first portion is generated for display, receive a second user input selecting a second EEG instance of the plurality of EEG instances;

in response to receiving the second user input, cross-reference the second EEG instance with the database to determine a second portion of the video data that corresponds to the first EEG instance; and replace, on the display device, the first portion with the second portion.

18. The system for correlating brain activity to physical manifestations of claim 11, wherein the control circuitry is further configured to:

generate a time stamp for the first instance that corresponds to a location in the received EEG data;

generate a time stamp for the first portion that corresponds to a location of the first portion in the video data; and determine that the time stamp for the first instance corresponds to the time stamp for the first portion.

19. The system for correlating brain activity to physical manifestations of claim 18, wherein the location in the received EEG data corresponds to a first sub-region of a plurality of sub-regions in a region of the display screen corresponding to a graphical representation of each EEG channel.

20. The system for correlating brain activity to physical manifestations of claim 19, wherein the first sub-region corresponds to the first instance that corresponds to a first EEG channel of the plurality of EEG channels and a second EEG instance that corresponds to a second EEG channel of the plurality of EEG channels.

* * * * *